United States Patent
Tong

(10) Patent No.: US 11,333,667 B2
(45) Date of Patent: May 17, 2022

(54) APPLICATIONS OF OPTICAL DETECTION OF LOW-LEVEL CHEMICAL AND BIOLOGICAL SUBSTANCES BY NONLINEAR LASER WAVE MIXING IN MEDICINE AND FOOD SAFETY

(71) Applicant: SAN DIEGO STATE UNIVERSITY FOUNDATION, San Diego, CA (US)

(72) Inventor: William G. Tong, La Jolla, CA (US)

(73) Assignee: SAN DIEGO STATE UNIVERSITY FOUNDATION, San Diego, CA (US)

(*) Notice: Subject to any disclaimer, the term of this patent is extended or adjusted under 35 U.S.C. 154(b) by 113 days.

(21) Appl. No.: 15/999,856

(22) PCT Filed: Feb. 21, 2017

(86) PCT No.: PCT/US2017/018752
§ 371 (c)(1),
(2) Date: Aug. 20, 2018

(87) PCT Pub. No.: WO2017/143347
PCT Pub. Date: Aug. 24, 2017

(65) Prior Publication Data
US 2021/0311067 A1   Oct. 7, 2021

Related U.S. Application Data

(60) Provisional application No. 62/303,328, filed on Mar. 3, 2016, provisional application No. 62/297,767, filed on Feb. 19, 2016.

(51) Int. Cl.
*G01N 33/58* (2006.01)
*B01L 3/00* (2006.01)
(Continued)

(52) U.S. Cl.
CPC ...... *G01N 33/582* (2013.01); *B01L 3/502715* (2013.01); *G01N 21/03* (2013.01);
(Continued)

(58) Field of Classification Search
CPC ........... G01N 33/582; G01N 27/44791; G01N 33/49; G01N 21/03; G01N 21/718;
(Continued)

(56) References Cited

U.S. PATENT DOCUMENTS 4,284,354 A   8/1981 Liao
4,355,897 A   10/1982 Kaye
(Continued)

FOREIGN PATENT DOCUMENTS

JP   WO2004027424 A1 * 1/2006 ........... G01N 33/582
WO   2000043742        7/2000
(Continued)

OTHER PUBLICATIONS

Gregerson, Marc, et al., "Ultrasensitive standoff chemical sensing based on nonlinear multi-photon laser wave-mixing spectroscopy", Proceedings of SPIE, 2012, vol. 8497, article No. 84970S, pp. 1-7.
(Continued)

*Primary Examiner* — Mohamed K Amara
(74) *Attorney, Agent, or Firm* — Perkins Coie LLP

(57) ABSTRACT

This patent document discloses techniques, systems, and devices for detecting a target substance using optical nonlinear wave mixing for enhanced detection sensitivity and accuracy. In one aspect, a method for measuring α-synuclein in a body fluid of a patient with high detection sensitivity and accuracy and providing early stage Parkinson's disease detection is provided. The method may comprise: supplying to a capillary analyte cell a fluidic sample that includes a body fluid of a patient containing α-synuclein, wherein the capillary analyte cell is located in a nonlinear optical four-
(Continued)

wave mixing device; directing laser light from the nonlinear optical four-wave mixing device into the capillary analyte cell to cause nonlinear optical four-wave mixing in the fluidic sample to generate a four-wave mixing signal that contains information on the α-synuclein in the fluidic sample; and processing the four-wave mixing signal to extract information on the α-synuclein in the fluidic sample.

27 Claims, 27 Drawing Sheets

Specification includes a Sequence Listing.

(51) Int. Cl.

| | | |
|---|---|---|
| G01N 21/03 | (2006.01) | |
| G01N 21/63 | (2006.01) | |
| G01N 21/71 | (2006.01) | |
| G01N 27/447 | (2006.01) | |
| G01N 33/49 | (2006.01) | |
| G01N 33/68 | (2006.01) | |

(52) U.S. Cl.
CPC ......... *G01N 21/636* (2013.01); *G01N 21/718* (2013.01); *G01N 27/44791* (2013.01); *G01N 33/49* (2013.01); *G01N 33/6896* (2013.01); *G01N 2021/0346* (2013.01); *G01N 2800/2835* (2013.01); *G01N 2800/56* (2013.01)

(58) Field of Classification Search
CPC ............ G01N 33/6896; G01N 21/636; G01N 2800/2835; G01N 2021/0346; G01N 2800/56; B01L 3/502715
See application file for complete search history.

(56) References Cited

U.S. PATENT DOCUMENTS

| | | | |
|---|---|---|---|
| 4,540,283 | A | 9/1985 | Bachalo |
| 4,622,642 | A | 11/1986 | Bajard et al. |
| 4,662,642 | A | 5/1987 | Archibald et al. |
| 4,728,165 | A | 3/1988 | Powell et al. |
| 4,854,705 | A | 8/1989 | Bachalo |
| 5,166,507 | A | 11/1992 | Davis et al. |
| 5,262,947 | A | 11/1993 | Boudan et al. |
| 5,600,444 | A | 2/1997 | Tong |
| 6,141,094 | A | 10/2000 | Tong |
| 6,248,540 | B1 | 6/2001 | Weinberg et al. |
| 8,268,551 | B2 | 9/2012 | Tong |
| 9,244,005 | B2 | 1/2016 | Tong |
| 2001/0033375 | A1 | 10/2001 | Mcfarland et al. |
| 2002/0015150 | A1 | 2/2002 | Armstrong et al. |
| 2003/0174324 | A1 | 9/2003 | Sandstrom |
| 2006/0263777 | A1 | 11/2006 | Tong |
| 2008/0171757 | A1* | 7/2008 | Eaton ................ G01N 33/5005 514/263.37 |
| 2008/0204043 | A1* | 8/2008 | Wang ..................... G01N 35/08 324/633 |
| 2008/0212166 | A1 | 9/2008 | Lett et al. |
| 2008/0264792 | A1 | 10/2008 | Moon et al. |
| 2021/0311067 | A1 | 10/2021 | Tong |
| 2022/0003676 | A1* | 1/2022 | Mazed ................ G01N 21/6454 |

FOREIGN PATENT DOCUMENTS

| | | | |
|---|---|---|---|
| WO | 2004068087 | A2 | 8/2004 |
| WO | WO-2010007630 | A1 * | 1/2010 ................ G01J 3/10 |
| WO | 2010120391 | A9 | 12/2010 |
| WO | 2017143347 | A1 | 8/2017 |

OTHER PUBLICATIONS

Hetu, Marcel, et al., "Zepto-mole detection in microfluidics by novel nonlinear multi-photon laser wave-mixing spectroscopy for biomedical and environmental applications", Proceedings of SPIE, 2014, vo. 9193, article No. 91930T, pp. 1-7.

Iwabuchi, Manna, et al., "Nonlinear multi-photon laser wave-mixing optical detection in microarrays and microchips for ultrasensitive detection and separation of biomarkers for cancer and neurodegenerative diseases", Proceedings of SPIE, 2015, vol. 9579, article No. 957904, pp. 1-7.

Iwabuchi, Manna F., et al., "Sensitive analysis of arsynuclein by nonlinear laser wave mixing coupled with capillary electrophoresis", Analytical Biochemistry, vol. 500 (2016) pp. 51-59.

Maxwell, Eric J., et al., "Sensitive detection of malachite green and crystal violet by nonlinear laser wave mixing and capillary electrophoresis", Journal of Chromatography B, vol. 1020 (2016) pp. 29-35.

Berniolles, S., et al., "Sensitive Absorption-Based Wave-Mixing Detector for Anthracycline Drugs Separated By Capillary Electrophoresis," Department of Chemistry and Biochemistry, San Diego State University, CEDau.doc.

Kan, Hongjing, et al., "Sensitive Analysis of Carotenoids By Liquid Chromatograpgy using Forward-Scattering Wave-Mixing Detection," LC-Car.doc, SDSU, Department of Chemistry and Biochemistry, 20 pages.

Lopez, Mirna M., et al., "Ultrasensitive Detection of Proteins and Antibodies by Absorption-Based Laser Wave-Mixing Detection Using a Chromophore Label," CBBprotein.doc., SDSU, 22 pages.

Nunes, Jon A., et al. "Wave-Mixing Circular Dichroism Detector for Chiral Liquid Chromatography," CD-LC.doc, SDSU, 23 pages.

L. Pibida et al. 'Laser resonance ionization mass spectrometry measurements of cesium in nuclear burn-up and sediment samples', Applied Radiation and Isoteses vol. 60, Issues 2-4, pp. 567-570, 2004.

Lopez, M.M., et al., "Laser wave-mixing optical method for sensitive detection of analytes in micro arrays and microchips," Proc. SPIE, 5591:185-189, Dec. 2004.

International Search Report and Written Opinion dated Feb. 9, 2005 for International Patent Application No. PCT/US2004/002409 (7 pages).

Andrews, J.M., et al., "Atomic flame spectrometry based on polarization-modulated optical phase conjugation by resonant degenerate four-wave mixing," Spectrochimica Acta Part B: Atomic Spectroscopy, 44B(1):101-107, 1989.

Andrews, J.M., et al., "Doppler-Free Spectrum of the Barium 1S0-1P1 Transition by Degenerate Four-Wave Mixing Using an Air/Acetylene Flame," Applied Spectroscopy, 45(4):697-700, 1991.

Atherton, A.A., et al., "Ultrasensitive absorption detection of protein and DNA microarrays based on nonlinear multi-photon wave-mixing spectroscopy," Proc. SPIE, 5969:59690, Sep. 2005.

Bao, X., et al., "Excited-state optical storage study in a dye-doped film using four-wave mixing spectroscopy," Proc. SPIE, 2998:343-347, Jan. 1997.

Bao, X., et al., "Optical Nonlinearity and Multiplex Holographic Storage in Azo Side-Chain Liquid Crystalline Polymer," Proc. SPIE, 3474:183-189, Oct. 1998.

Berniolles, S., et al., "Diode laser-based nonlinear degenerate four-wave mixing analytical spectrometry," Spectrochimica Acta Part B: Atomic Spectroscopy, 49B(12-14): 1473-1481, Oct.-Dec. 1994.

Berniolles, S., et al., "Low-power compact laser-based nonlinear degenerate four-wave mixing detection for flowing liquids," Proc. SPIE, 2546:145-151, Sep. 1995.

Berniolles, S., et al., "Sensitive absorbance measurement for gas-phase analytes based on multiwave mixing spectroscopy," Proc. SPIE, 2835:248-254, Nov. 1996.

Berniolles, S., et al., "Sensitive Capillary-Based on-Column Detection Method By Laser Wave Mixing," Proc. SPIE, 2980:127-132, May 1997.

Berniolles, S., et al., "Sensitive on-Column Absorbance Detection of Native Molecules," Proc. SPIE, 3270:200-206, May 1998.

Briggs, R., et al., "Sub-Doppler high-resolution wave-mixing detection method for isotopes in environmental applications," Proc. SPIE, 5586:54-59, Dec. 2004.

(56) References Cited

OTHER PUBLICATIONS

Chen, D.A., et al., "High-resolution Laser Spectroscopy Based on Polarisation-modulated Optical Phase Conjugation in a Demountable Cathode Discharge," J. Anal. Atomic Spectrometry, 3:531-535, Jun. 1988.
International Search Report and Written Opinion dated Oct. 29, 2010 for International Application No. PCT/US2010/020682, filed Jan. 11, 2010 (11 pages).
Kan, H., et al., "Sensitive wave-mixing detectors for capillary electrophoresis and liquid chromatography," Proc. SPIE, 2835:135-142, Nov. 1996.
Knittle, J.E., et al., "Sensitive detection of enzyme activity by multi-photon nonlinear laser spectroscopy," Proc. SPIE, 5587:177-182, Nov. 2004.
Luena, G.A., et al., "Doppler-Free Laser Polarization Spectroscopy Using a Demountable DC Cathode Discharge Cell as a Trace Concentration Atomizer," Applied Spectroscopy, 44(10): 1668-1672, Nov. 1990.
Lyons, W., et al., "Nonlinearwave-mixing spectroscopy for sub-Doppler isotope analysis with trace-level detection sensitivity," Proc. SPIE, 5971:597109, Sep. 2005.
Maniaci, M.J., et al., "Multiphoton laser wave-mixing absorption spectroscopy for samarium using a graphite furnace atomizer," Spectrochimica Acta Part B, 59(7):967-973, Jul. 2004.
Mann, B.A., et al., "Detection and imaging of nitrogen dioxide with the degenerate four-wave-mixing and laser-induced-fluorescence techniques," Applied Optics, 35(3):475-481, Jan. 1996.
Mickadeit, F., et al., "Sensitive Sub-Doppler Nonlinear Spectroscopy for Hyperfine Structure Analysis Using Simple Atomizers," Proc. SPIE, 3270:168-173, May 1998.
Mickadeit, F.K., et al., "Sub-Parts-Per-Quadrillion-Level Graphite Furnace Atomic Absorption Spectrophotometry Based on Laser Wave Mixing," Anal. Chem., 76(6):1788-1792, Mar. 2004.
Neyer, D.W, et al., "Circular Dichroism Spectroscopy Using Coherent Laser-Induced Thermal Gratings," J. American Chemical Society, 119(35):8293-8300, 1997.
Nunes, J., et al., "Optical Fiber-Based Wave-Mixing Probe," Proc. SPIE, 2980:429-433, May 1997.
Nunes, J.A., et al., "Circular Dichroism Spectroscopy by Four-Wave Mixing Using Polarization Grating-Induced Thermal Gratings," J. Phys. Chem. A, 101 (18):3279-3283, 1997.
Nunes, J.A., et al., "Optical Fiber-Based Wave Mixing as a Convenient and Sensitive Laser Analytical Tool for Condensed-Phase Analytes," Applied Spectroscopy, 52(5):763-769, 1998.
Nunes, J., et al., "Sensitive Circular Dichroism Spectroscopy Based on Nonlinear Degenerate Four-Wave Mixing," Anal. Chem., 65(21):2990-2994, Nov. 1993.
Nunes, J. A., et al., "Sensitive laser wave-mixing detection methods for biomedical applications," Proc. SPIE, 2388:205-212, May 1995.
Tong, W.G., et al., "Doppler-Free Spectroscopy Based on Phase Conjugation by Degenerate Four-Wave Mixing in Hollow Cathode Discharge," Applied Spectroscopy, 41(4):586-590, 1987.
Tong, W.G., et al., "Laser Spectrometry Based on Phase Conjugation by Resonant Degenerate Four-Wave Mixing in an Analytical Flame," Anal. Chem., 59(6):896-899, Mar. 1987.
Weed, K.M., et al., "Sensitive sub-Doppler multi wave-mixing spectroscopy for flame and graphite furnace atomizers," Proc. SPIE, 2385:157-164, Apr. 1995.
Weed, K.M., et al., "Trace Analysis of Rubidium Hyperfine Structure in a Flame Atomizer Using Sub-Doppler Laser Wave-Mixing Spectroscopy," Applied Spectroscopy, 57(12):1455-1460, Dec. 2003.
Wu, Z., et al., "Absorbance detection of amino acids by laser wave mixing in microbore liquid chromatography," J. of Chromatography A, 805(1-2):63-69, May 1998.
Wu, Z., et al., "Doppler-free measurement of the calcium 4s2 1S0—4s4p 1p1 transition at 422.673 nm by degenerate four-wave mixing in a demountable cathode discharge atomizer," Spectrochimica Acta Part B, 47B(3):449-457, Mar. 1992.
Wu, Z., et al., "Forward-Scattering Degenerate Four-Wave Mixing as a Simple Sub-Attomole-Sensitive Nonlinear Laser Analytical Spectrometric Method," Anal. Chem., 65(2):112-117, Jan. 1993.
Wu, Z., et al., "Laser Analytical Spectrometry Based on Optical Phase Conjugation by Degenerate Four-Wave Mixing in a Flowing Liquid Analyte Cell," Anal. Chem., 61(9):998-1001, May 1989.
Wu, Z., et al., "Sensitive absorbance detection method for capillary electrophoresis based on laser wave-mixing," J. of Chromatography A, 773:291-298, 1997.
Wu, Z., et al., "Sensitive absorbance measurement method based on laser multi-wave mixing," Spectrochimica Acta Part B, 49B(12-14):1483-1489, Oct.-Dec. 1994.
Wu, Z., et al., "Stable Isotope Ratio Analysis at Trace Concentrations Using Degenerate Four-Wave Mixing with a Circularly Polarized Pulsed Probe Beam," Anal. Chem., 63(9):899-903, May 1991.
Wu, Z., et al., "Trace-Concentration Detection of Cobalt in a Liquid Flow Cell By Degenerate Four-Wave Mixing Using Low-Power Off-Resonant Laser Excitation," Anal. Chem., 63(18):1943-1947, Sep. 1991.
Alderman, D.J., "Malachite green: a review," J. Fish Diseases 8 (1985) 289-298.
Andersen, J.E., et al., "Determination of malachite green and leucomalachite green in salmon with in-situ oxidation and liquid chromatography with visible detection," FDA Lab. Info. Bulletin 20 (2004), No. 4334.
Commission Decision 2004/25/EC as regards the setting of minimum required performance limits (MRPLs) for certain residues in food of animal origin. Off. J. Euro. Union L6 (2004) 38-39.
Culp, S. J., et al., "Malachite green: a toxicological review", J. Am. Coll. Toxicol. 15 (1996) 291-238.
Srivastava, S., et al., "Toxicological Effects of Malachite Green" Aquatic Toxicology 66 (2004) 319-329.
Safarik, I. et al., "Detection of Low Concentrations of Malachite Green and Crystal Violet in Water" Water Research 36 (2002) 196-200.
Rand, K. N., "Crystal Violet Can Be Used to Visualize DNA Bands During Gel Electrophoresis and to Improve Cloning Efficiency." Tech. Tips Online 1 (1996).
Andersen, W. C. et al., "Quantitative and Confirmatory Analyses of Malachite Green and Leuco malachite Green Residues in Fish and Shrimp." J. Agric. Food Chem. 54 (2006) 4517-4523.
Dowling, G., et al., "Confirmatory analysis of malachite green, leucomalachite green, crystal violet and leucocrystal violet in salmon by liquid chromatography-tandem mass spectrometry." Analytica Chimica Acta 586 (2007) 411-419.
Bueno, M., et al., "Determination of Malachite Green Residues in Fish Using Molecularly Imprinted Solid-Phase Extraction Followed by Liquid Chromatography-Linear Ion Trap Mass Spectrometry." Analytica Chimica Acta 665 (2010) 47-54.
Xu, Y., et al., "Simultaneous Determination of Malachite Green, Crystal Violet, Methylene blue and the Metabolite Residues in Aquatic Products by Ultra-Performance Liquid Chromatography with Electrospray Ionization Tandem Mass Spectrometry." J. Chrom. Sci. 50 (2012) 591-597.
Tan, E., et al., "Three Dimensional Design of Large-Scale TiO2 Nanorods Scaffold Decorated by Silver Nanoparticles as SERS Sensor for Ultrasensitive Malachite Green Detection." ACS Appl. Mater. Interfaces 4 (2012) 3432-3437.
Xu, H., et al., "Monoclonal antibody-based enzyme-linked immunosorbent assay for detection of total malachite green and crystal violet residues in fishery products." Intern. J. Environ. Anal. Chem. iFirst (2012) 1-11.
Bilandzic, N., et al., "Malachite green residues in farmed fish in Croatia." Food Control 26 (2012) 393-396.
Tsai, C. Tsai, et al., "Optimization ofthe Separation of Malachite Green in Water by Capillary Electrophoresis Raman Spectroscopy (CE-RS) Based on the Stacking and Sweeping Modes." Talanta 72 (2007) 368-372.
Jiang, T., et al., "Analysis of Malachite Green, Gentian Violet and their Leuco Metabolites in Catfish and Carp by Micellar Electrokinetic Capillary Chromatography." Food and Drug Analysis 20 (2012) 94-100.

(56) References Cited

OTHER PUBLICATIONS

Maleki, R., et al., "Trace determination of malachite green in water samples using dispersive liquid-liquid microextraction coupled with high-performance liquid chromatography-diode array detection." Intern. J. Environ. Anal. Chem. 92 (2012) 1026-1035.

Sun, H., et al., "Capillary electrophoresis combined with accelerated solvent extraction as an improved methodology for effective separation and simultaneous determination of malachite green, crystal violet and their leuco-metabolites in aquatic products." Anal. Methods 5 (2013) 267-272.

Sadri, B., "Protein Analysis at the Single Cell Level by Nonlinear Laser Wave-Mixing Spectroscopy for High Throughput Capillary Electrophoresis Applications." Ph. D. Dissertation, North Carolina State University (2008).

Andersen, W.C., et al., "Multiresidue method for triphenylmethane dyes in fish; Malachite green, crystal (gentian) violet, and brilliant green." Analytica Chimica Acta 637 (2009) 279-289.

Hetu, M., et al., "Zepto-mole detection in microfluidics by novel nonlinear multi-photon laser wave-mixing spectroscopy for biomedical and environmental applications." Proc. of SPIE 9193 (2014) 91930T.

Mikkers, F.E.P., et al., "High-Performance Zone Electrophoresis." J. Chrom. 169 (1979) 11-20.

Maxwell, E., et al., "Sensitive Detection of Malachite Green and Crystal Violet by Nonlinear Laser Wave Mixing and Capillary Electrophoresis." Dept. of Chem. and Biochemistry, San Diego State University, Feb. 29, 2016 MG CV 15 Maxwell Tong 1508 JChrom 1601 Manuscript.

\* cited by examiner

```
        10              20              30
MDVFMKGLSK      AKEGVVAAAE      KTKQGVAEAA 40              50              60
GKTKEGVLYV      GSKTKEGVVH      GVATVAEKTK 70              80              90
EQVTNVGGAV      VTGVTAVAQK      TVEGAGSIAA 100             110             120
ATGFVKKDQL      GKNEEGAPQE      GILEDMPVDP 130             140
DNEAYEMPSE      EGYQDYEPEA
```

FIG. 6

APPLICATIONS OF OPTICAL DETECTION OF LOW-LEVEL CHEMICAL AND BIOLOGICAL SUBSTANCES BY NONLINEAR LASER WAVE MIXING IN MEDICINE AND FOOD SAFETY

PRIORITY CLAIMS AND CROSS-REFERENCE TO RELATED APPLICATIONS

This patent document is a 371 of International Application No. PCT/US2017/018752, filed Feb. 21, 2017, which claims priority to and the benefit of Provisional Patent Application No. 62/297,767, filed on Feb. 19, 2016 and Provisional Patent Application No. 62/303,328, filed on Mar. 3, 2016. The disclosure of the above applications is incorporated herein by reference for all purposes as if fully set forth herein.

STATEMENT REGARDING FEDERALLY SPONSORED RESEARCH OR DEVELOPMENT

Part of the inventions in this patent document was made with United States government support under Grant Nos. 5-R01-GM41032 and 2R25GM058906-13 awarded by the National Institutes of Health (NIH)/National Institute of General Medical Sciences (NIGMS). In addition, part of the inventions was made with United States government support by the National Institute of General Medical Sciences, National Institutes of Health under Grant 5-R01-GM41032, the National Science Foundation, the U.S. Department of Homeland Security Science and Technology Directorate, the U.S. Department of Defense (CCAT), the Army Research Office, and the NIH NIGMS SDSU IMSD Program Grant 2R25GM058906-13. The United States government has certain rights in the inventions.

SEQUENCE LISTING

This application contains a Sequence Listing, which was submitted in ASCII format via EFS-Web and is hereby incorporated by reference in its entirety. The ASCII copy, created on May 16, 2021, is named Sequence Listing 009077-8006.US01 ST25 and is 2 KB in size.

TECHNICAL FIELD

This patent document relates to methods, techniques and devices for optical detection of low-level chemical and biological substances based on optical nonlinear wave mixing for enhanced detection sensitivity and accuracy.

BACKGROUND

Accurate detection of low-level substances are technically difficult even in well-controlled scientific laboratory conditions and presents a challenge in practical applications in various fields such as medicine and detection of chemical or biological substances. Over the decades, optical sensing technologies have been explored to address the technical challenges in accurate detection of low-level substances. Nonlinear optical wave mixing techniques are among the different sensitive detection technologies that under investigation.

SUMMARY

This patent document discloses optical sensing techniques, systems, and devices for detecting a target substance using optical nonlinear wave mixing for enhanced detection sensitivity and accuracy.

In one aspect, a method is provided for measuring $\alpha$-synuclein in a body fluid of a patient with high detection sensitivity and accuracy and providing early stage Parkinson's disease detection. For example, such a method can be implemented to include supplying to a capillary analyte cell a fluidic sample that includes a body fluid of a patient containing $\alpha$-synuclein, wherein the capillary analyte cell is located in a nonlinear optical four-wave mixing device; directing laser light from the nonlinear optical four-wave mixing device into the capillary analyte cell to cause nonlinear optical four-wave mixing in the fluidic sample to generate a four-wave mixing signal that contains information on the $\alpha$-synuclein in the fluidic sample; processing the four-wave mixing signal to extract information on the $\alpha$-synuclein in the fluidic sample; and using the extracted information to determine the patient's condition in connection with the Parkinson's disease.

In another aspect, an optical sensing based system is provided for diagnosing a person's condition in connection with the Parkinson's disease. For example, such a system can be implemented to include a microfluidic system that includes a capillary analyte cell that is coupled to receive a fluidic sample that includes a body fluid of a patient containing $\alpha$-synuclein; a nonlinear optical four-wave mixing device that includes a laser that produces laser beams for nonlinear four-wave mixing, optical elements that direct the laser beams to a selected location in the capillary analyte cell where the laser beams intercept with one another to interact with the fluidic sample in the capillary analyte cell to cause nonlinear wave mixing that generates a four-wave mixing signal that contains information on the $\alpha$-synuclein in the fluidic sample, and an optical detector that receives the four-wave mixing signal and converts the received four-wave mixing signal to a detector signal; and a processing module that processes the detector signal to extract information on the $\alpha$-synuclein in the fluidic sample and uses the extracted information to determine the patient's condition in connection with the Parkinson's disease.

In another aspect, a method is provided for measuring a low concentration level of a suspect or target substance such as Malachite Green and Crystal Violet with high detection sensitivity and accuracy. For example, such a method can be implemented to include supplying to a capillary electrophoresis system a fluidic sample that includes a low concentration of a suspect substance within a nonlinear optical four-wave mixing device; directing laser light from the nonlinear optical four-wave mixing device into the fluidic sample to cause nonlinear optical four-wave mixing in the fluidic sample to generate a four-wave mixing signal that contains information on the low concentration of the suspect substance in the fluidic sample; and processing the four-wave mixing signal to extract information on the suspect substance in the fluidic sample.

In yet another aspect, a device is provided for measuring a low concentration level of a suspect substance such as Malachite Green and Crystal Violet with high detection sensitivity and accuracy. For example, such as device can be implemented to include a microfluidic system that is coupled to receive a fluidic sample that includes a fluidic sample that includes a low concentration of a suspect substance; a nonlinear optical four-wave mixing device that includes a laser that produces laser beams for nonlinear four-wave mixing, optical elements that direct the laser beams to a selected location in microfluidic system where the laser beams intercept with one another to interact with the fluidic sample to cause nonlinear wave mixing that generates a four-wave mixing signal that contains information on the suspect substance in the fluidic sample, and an optical detector that receives the four-wave signal and converts the received four-wave mixing signal to a detector signal; and a processing module that processes the detector signal to extract information on the suspect substance in the fluidic sample.

The above and other aspects and their implementations are described in greater detail in the drawings, the description and the claims.

BRIEF DESCRIPTION OF THE DRAWINGS

FIG. 6 shows amino acid sequence of α-synuclein (SEQ ID NO: 1).

DETAILED DESCRIPTION

Figure 1:
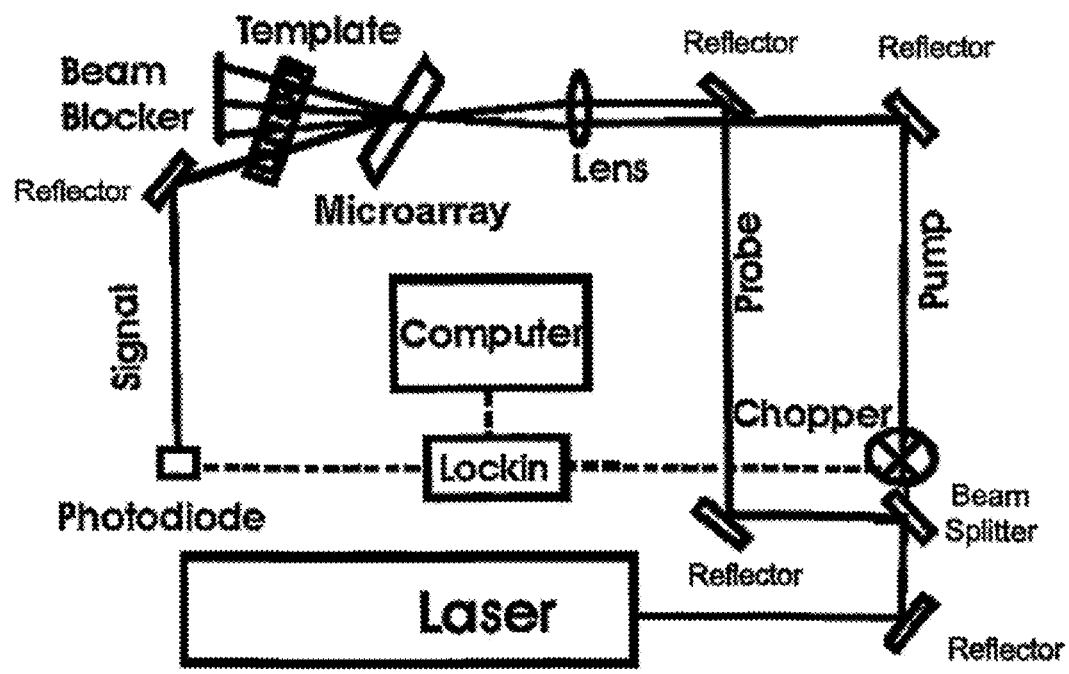
FIGS. 1, 2A, 2B, 2C, 2D and 2E show examples of nonlinear optical wave mixing based optical sensing devices for measuring target substances.

This patent document discloses optical sensing techniques and devices based on nonlinear wave mixing to detect a target substance and to enhance detection sensitivity and accuracy that are difficult or impossible to achieve with some other detection techniques or devices.

The optical sensing technology employed in various implementations of the disclosed technology is based on nonlinear laser wave-mixing spectroscopy techniques that offer excellent detection sensitivity for chemical or biomedical applications, including early diagnosis and investigation of neurodegenerative diseases.

Nonlinear wave mixing can be in various configurations by mixing different number of laser beams. Consider nonlinear four-wave mixing as an example which is an optical process in an optical medium where three coherent optical waves interact with one another through nonlinear coupling to produce a fourth coherent signal wave. The nonlinearities of the medium, primarily the third-order nonlinear susceptibility of the medium in some implementations, contribute to such nonlinear coupling. The signal wave includes information on optically-excited atoms or molecules present in the medium where the three input optical waves intersect and hence can be collected to extract information about the medium. The strength of the signal wave is associated with the population of atoms or molecules and the spectral characteristics of the signal wave can be analyzed to reveal the structure of the atoms or molecules of interest. The coherent characteristics of the four-wave mixing signal beam have a number of advantages, including a laser-like signal beam, efficient signal collection, excellent spatial resolution, and sub-Doppler spectral resolution. Hence, four-wave mixing has been widely used as a highly sensitive tool in spectroscopic measurements.

Optical sensing devices and techniques described in this document are designed for highly sensitive, selective and high-resolution sensing of various materials based on nonlinear laser wave mixing. Exemplary implementations of nonlinear wave mixing for measurements based on backward and forward scattering nonlinear wave mixing, e.g., four-wave mixing configurations, are described. Nonlinear optical wave mixing may be implemented in optical sensing systems with different configurations. For example, U.S. Pat. No. 5,600,444 entitled "Detecting Analyte Light Absorption Utilizing Degenerate Four-wave Mixing" to Tong describes devices and techniques for using two-input-beam forward-scattering degenerate four-wave mixing to achieve ultrasensitive analytical measurements of an analyte. Backward-scattering degenerate four-wave mixing has also be used for sensitive laser spectroscopic detection. See, e.g., U.S. Pat. No. 6,141,094 entitled "Sensitive Laser Spectroscopic Detection Based on Three-Dimensional Nonlinear Four-Wave Mixing" to Tong.

In particular, nonlinear optical wave mixing in forward wave mixing and backward wave mixing configurations can be used to detect target substances in liquid-phase samples by using capillary electrophoresis devices and other liquid sample handling devices to achieve high detection sensitivity and accuracy. See U.S. Pat. No. 8,268,551B2 entitled "Sensitive Sensing Based on Optical Nonlinear Wave Mixing" to Tong (previously published as U.S. Patent Publication No. US 2006-0263777 A1); and U.S. Pat. No. 9,244,005 entitled "Ultrasensitive detection of isotopes, chemical substances and biological substances using laser wave-mixing detectors" to Tong.

The entire disclosures of the above referenced patent documents are incorporated by reference as part of the disclosure of this document. Techniques and features in the above-referenced patents may be used or combined with the techniques described in this document.

Nonlinear wave mixing techniques for sensitive high-resolution detection may be implemented for detecting substances in various material forms. For example, high temperature atomizers may be used to perform the nonlinear optical wave mixing in a gas such as graphite discharge plasmas, graphite furnace, inductively coupled plasma, and flame atomizers with detection sensitivity levels in the sub-parts-per-quadrillion levels. Applications to liquid-phase samples can achieve high detection sensitivity levels. The laser wave mixing methods offer many potential applications in many fields including chemistry, biology, and medicine. For example in biotechnology, laser wave mixing could be used for detecting biomolecules (e.g., proteins, DNAs, etc.) with or without labels or tags, for studying enzyme activities, for monitoring smaller chemical/biological changes more dramatically with less tedious procedures, for studying bio molecular structures, for analysis of small bio cells with high spatial resolution, for sensitive detection as sensors, and many other potential applications.

The laser wave mixing based detection methods may be useful for various applications in a wide range of fields for measuring atoms, isotopes (gas-phase) and molecules (liquid-phase) at detection levels that may be difficult to achieve with other sensing techniques. For example, laser wave mixing may be used to improve the detection sensitivity by a factor of about 1,000 to 1,000,000 relative to other sensing techniques. For example, preliminary detection limits for laser wave mixing may be obtained at sub-parts-per-quadrillion level, sub-attogram, sub-zeptomole, and sub-femto molar detection limits. Laser wave mixing may be effectively interfaced to popular gas-phase atomizers and liquid-phase flow systems for highly sensitive detection of e.g., gas-phase atoms and isotopes, at sub-Doppler spectral resolution and sensitive detection of liquid samples. In various implementations, laser wave mixing may be interfaced with a wide range of chemical instruments for holding or handling the samples. Examples of the instruments include, but are not limited to, gas chromatographs (GC), liquid chromatographs (LC), mass spectrometers (MS), GC-MS, LC-MS, inductively coupled plasmas (ICP), ICP-MS, high performance/power capillary electrophoresis (HPCE) systems, flow injection analysis (FIA) systems.

In nonlinear optical wave mixing, the generated nonlinear wave-mixing signal has a nonlinear and strong dependence on the input laser power (mainly the pump laser power), e.g., a four-wave-mixing signal in general has a cubic dependence on the input laser power. The signal strength, and hence, the detection sensitivity can be further enhanced by using higher input beam intensities up to about the saturation intensity of the nonlinear optical material or the target substance to be detected. In the example of a four-wave mixing device, the four-wave-mixing signal has a quadratic dependence on absorption coefficient. For analytes with low absorption coefficients, the wave-mixing detection sensitivity can be comparable to or better than those of conventional laser methods because of the nonlinear signal properties such as the nonlinear optical power dependence, high signal collection efficiency (virtually 100% optical collection efficiency in some four-wave mixing devices), and the laser-like coherence properties of the nonlinear optical signal beam. For example, unlike laser-induced fluorescence methods where the signal is a small fraction of a widely diffused fluorescence signal laser, the wave-mixing signal is a collimated coherent laser-like beam and hence nearly the entire signal beam can be directed into a photodetector. Furthermore, since wave mixing is an absorption method, both fluorescing and non-fluorescing analytes can be measured.

FIG. 1 shows an exemplary nonlinear optical four-wave mixing detection device that combines a forward-scattering degenerate four-wave mixing sensor with a microarray for detecting chemical or biological materials in the microarray cells. A laser such as an argon ion laser or other suitable laser with the desired laser wavelength is used to produce an input laser beam. The input beam is split into a pump beam and a probe beam via a beam splitter, e.g., with a ratio of 70:30. The pump and probe beams are then recombined and focused on the microarray slide (a microchip, a capillary channel, a waveguide, or a microfluidic device). A template with prearranged holes is placed at the back of the microarray to block all the other optical beams and to only allow the signal beam to pass through to reach a photodetector which receives the signal beam.

Figure 2A:
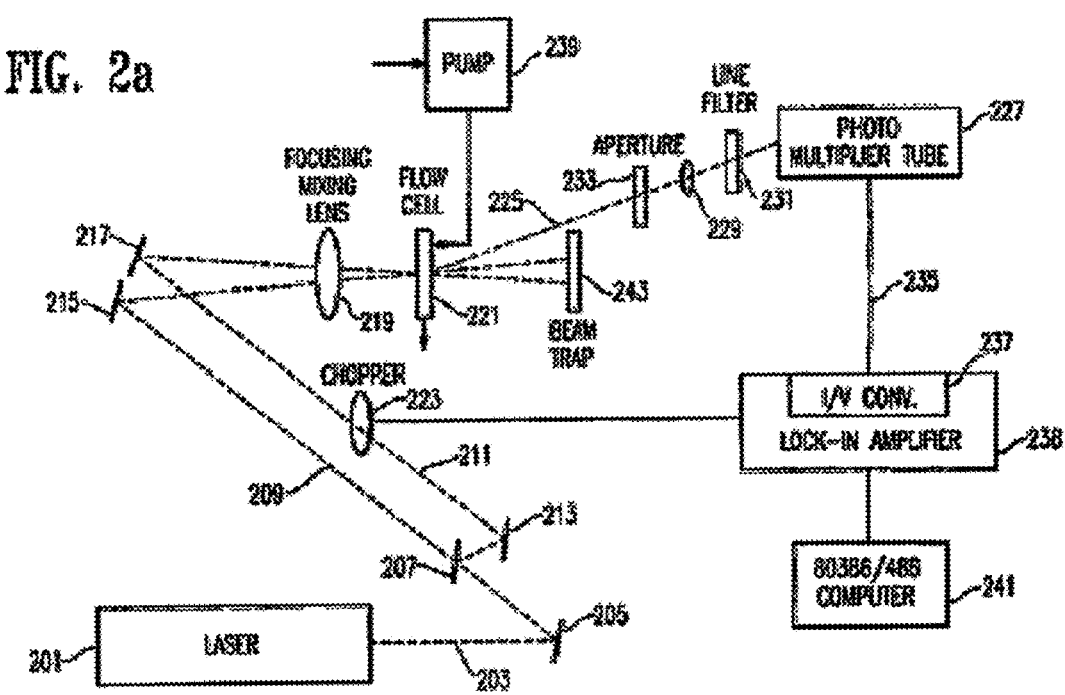

FIG. 2a shows one example of a two-input-beam forward-scattering degenerate four-wave mixing F-D4WM arrangement. It should be understood that the particular arrangement of reflectors and beam splitters is provided only as an exemplar only. This system includes an excitation light source 201, which may be a compact diode laser, such as is commonly known. Alternatively, a helium-neon laser, a continuous-wave argon ion laser or a Nd:YAG laser may be used. A laser beam 203 output by the light source 201 is preferably reflected by a reflector 205 and split by a beam splitter 207 to form a first 209 and a second 211 input beam. The second input beam 211 is reflected by a second reflector 213 such that the first 209 and second 211 input beams are preferably generally parallel. The intensity 11, of the first input beam 209 with respect to the intensity 12 of the second input beam 211 arriving at the sample cell, 11:12, is approximately 7:3 to generate the signal in one direction only. The preferred ratio is 1:1 to generate two signal beams, if desired.

A third reflector 215 and a fourth reflector 217 redirect the first input beam 209 and the second input beam 211, respectively, toward a single 100-mm focusing lens 219. The focusing lens 219 preferably focuses and mixes both input beams 209, 211. A sample holder 221 is placed at the lens' focal point. The sample holder 221 may be a DNA microarray chip, a sample cell, or other devices holding the sample under measurement. The diameter of both the first input beam spot and the second input beam spot on the sample cell 221 may be approximately 34 micros as one example. The first input beam 209 and the second input beam 211 intersect inside the sample cell 221 with an intersect angle which may be approximately 1.5 degrees or less. The small input beam spots allow the system to interface directly with systems in which an analyte is available in a small volume, such as a cell in a microarray chip, the capillary tube of a high power/high performance capillary electrophoresis system (HPCE), the column of a high performance liquid chromatography (HPLC) system, or to directly probe a small volume inside a gas-phase atomizer such as flame, dc plasma, graphite furnace, inductively coupled plasma, with high spatial resolution in diagnostic studies.

In order to optimize the signal strength of a phase-conjugate signal which is generated, the difference in path lengths (or distances traveled) for first input beam 209 and the second input beam 211 are preferably kept to less than the coherence length of the laser. A device for amplitude modulating the second input beam 211, such as a mechanical light chopper 223 (for example, Model 03-OC4000, manufactured and distributed by Photon Technology International Inc., Princeton, N.J.), or any solid state electronic light intensity modulation device, is used. A phase-conjugate signal beam 225 generated in the sample cell 221 is directed to a detector 227, such as a photomultiplier tube (e.g., Model R928, manufactured and distributed by Hamamatsu Corp., Middlesex, N.J.) after passing through a lens 229 preferably having a 250-mm focal length and preferably a filter 231 which in the preferred embodiment is a 514.5 nm laser-line filter when using an argon ion laser. A small aperture 233 is preferably disposed in front of the detector 227 to minimize background noise due to the scattering of the two input beams 209 and 211.

The electrical output signal 235 of the detector 227 is then preferably coupled to a current-to-voltage converter 237, the output of which is preferably monitored by a lock-in amplifier (otherwise known as phase sensitive amplifier) 238 (such as Model 5207, manufactured and distributed by Princeton Applied Research, Princeton, N.J.). The output from the detector 227 may also be coupled to other processor components 241, such as a strip-chart recorder, personal computer including an analog to digital converter, or any other such processing device. Control of the present invention may be performed by the same computer used to control a HPCE, HPLC, or atomizer system with which the present invention is being used.

In implementations where the sample holder 221 is a cell, the sample cell 221 may be the capillary of an HPCE system, the column of an HPLC system, or a gas-phase atomizer system (e.g., flame, de plasma, ICP plasma, graphite furnace). However, a rectangular glass flow cell with approximately a 0.1-mm optical path length (such as a Type 48, manufactured and distributed by Starna Cells, Inc., Atascadero, Calif.) may be used to measure an analyte for other purposes. Naturally, the sample cell 221 may take any form which can hold a volume of analyte which is at least equal to the spot volume of the focused input beams 209, 211, and which allows the input beams 209, 211 to enter and the signal beam 225 to exit without excessive attenuation. Furthermore, the analyte in the sample cell 221 may be any substance in any phase (i.e., liquid, solid, or gaseous), such as eosin B dissolved in ethanol and iodine in carbon tetrachloride. The present system is capable of analyzing solids and gases, as well as liquids.

An analyte solution may be delivered to the sample cell 221 in accordance with the system with which the present invention is being used. For example, the analyte is delivered by electrophoresis in an HPCE system or a pump in a HPLC system. Alternatively, a pump, such as a peristaltic pump 239 may be used to deliver the analyte to the sample cell 221.

After the two input beams 209, 211 pass through the sample cell 221, they are blocked by a beam trap 243, and the signal beam 225 is easily separated and directed toward the detector 227. An analyte solution with a relatively high concentration may be used as an "alignment solution" to optimize the optical alignment. A micromolar-level solution can generate a strong signal that is visible to the naked eye, thus allowing simple alignment of the present invention. Signal optimization is performed simply by adjusting the mirrors and the lenses, and by carefully adjusting the position of the sample cell 221 so that the sample cell 221 is at the focal point of the wave-mixing lens, while observing the strength of the visible signal spot on a card (or on a photodetector for trace-concentration analytes). Of course, any other means for determining the maximum strength of the signal beam 225 while adjusting the alignment of the system would be equally acceptable. For example, a self-adjusting system using feedback from the lock-in amplifier 238 might be used to determine the optimum alignment of the system. Once the optical alignment is optimized, the alignment and the signal remain very stable and different analyte solutions could be flowed through and analyzed without any further adjustments.

Figure 2B:
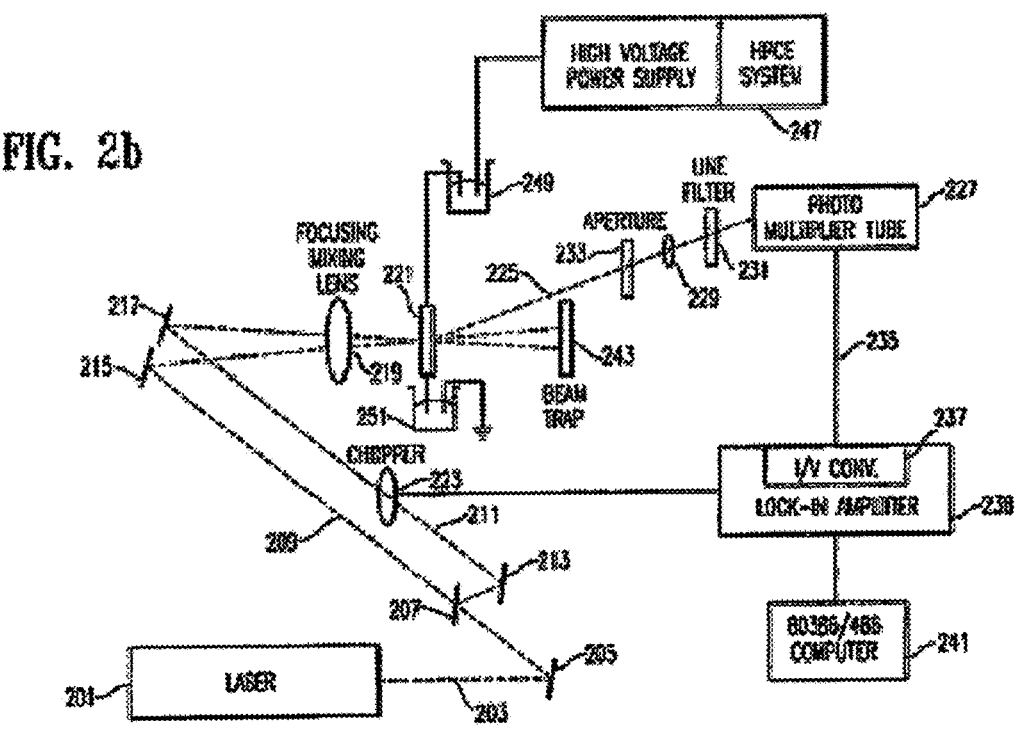

FIG. 2b illustrates an implementation two-input-beam wave mixing system coupled to the capillary tube of a HPCE system. The sample cell 221 is part of the capillary tube of the HPCE system. One end of the sample cell draws from a positive pool 249. The other end of the sample cell discharges into a negatively charged pool 251. A high voltage source is coupled to, and controlled by, the HPCE system controller 247.

Figure 2C:
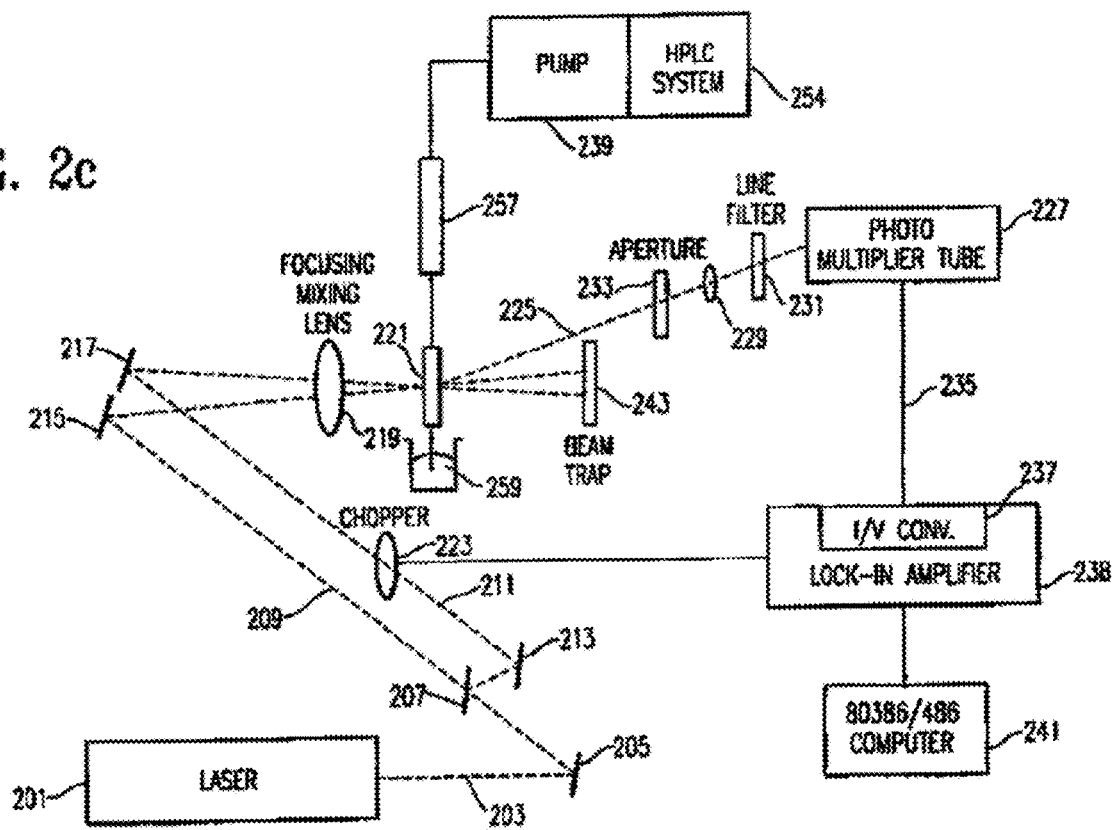

FIG. 2c illustrates another two-input-beam system coupled to a column 257 of a HPLC system. The sample cell 221 is coupled at one end to the column 257, and at the other end to a waste pool 259. A pump is coupled to, and controlled by, a HPLC system controller 255.

Figure 2D:
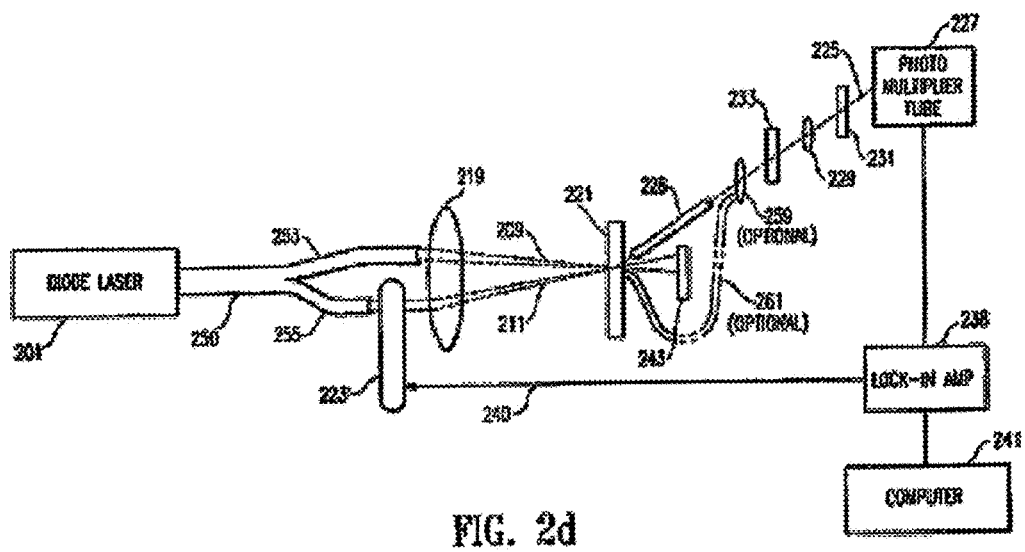

FIG. 2d further shows another example where the laser beams 209, 211, 225 are each transmitted through a fiber optic cable 250. Hence, transmission of laser light through air can be minimized. The fiber optic cable may be pre-aligned and bound to a substrate to prevent misalignment. The output of the laser source 201 may be coupled directly to the fiber optic cable 250 in known fashion. The fiber optic cable may be split into two sections 253, 255 in known fashion, thus dividing the beam into the first input beam 209 and the second input beam 211. The second section of fiber optic cable 255 may be coupled to an amplitude modulation device 2231, such as a well-known mechanical chopper, or any solid state electronic light intensity modulation device or an electro-optical modulator. Use of an electronic circuit for modulating the second input beam 211 allows the system to be produced in a compact package. The output of the first section of fiber optic cable 253 and the output from the modulation circuit 223' are preferably coupled to a lens 219. The lens causes the two input beams 209, 211 to be focused to a fine point within a sample cell 221. The input beams 209, 211 are preferably trapped at the opposite side of sample cell 221 by a beam trap 243. A signal beam 225 is generated within the sample cell 221 and projects outward through an aperture 233, a lens 229, a line filter 231, and into a photomultiplier tube 227. The path from the sample cell 221 to the photomultiplier tube 227 may, be through a fiber optic cable 228. Alternatively, the path may be through air. In one alternative embodiment of the present invention, two signal beams 225, 303 may be coupled to the photomultiplier tube 227 through a summing lens 259 by fiber optic cable 261, or each signal beam 225 and 303 may be coupled to a separate photomultiplier or photodiode, via air or fiber optic cables and detected by summing or multiplication.

Figure 2E:
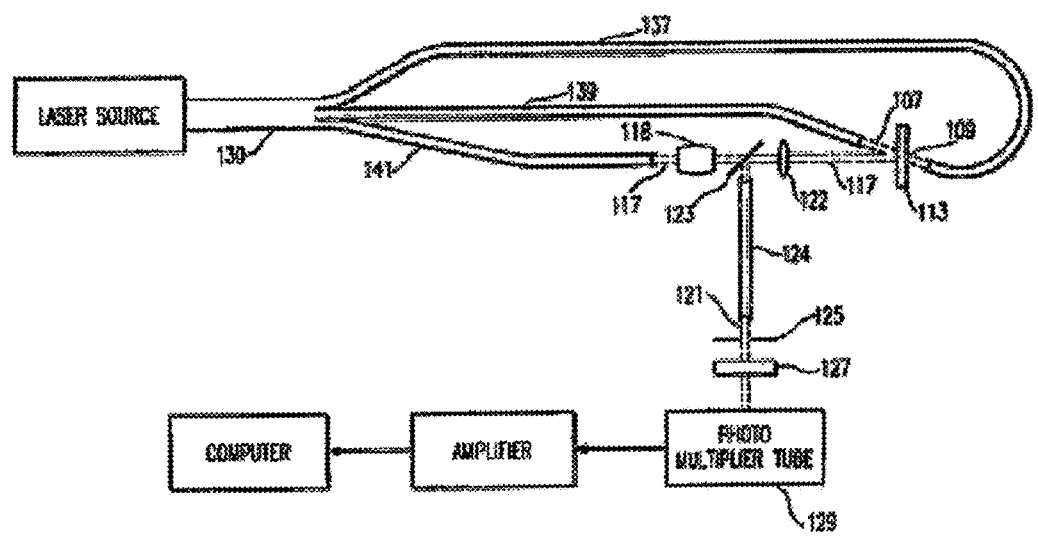

FIG. 2e shows one backward D4WM system having fiber optic cable to minimize alignment difficulties. A fiber optic cable 130 is divided into three 137, 139, 141 such that the signal is split into three beams 107, 109, 117. One input beam 107 is preferably directed to the sample cell 113 at the appropriate angle by the fiber optic cable 139. The second input beam 117 is directed by the fiber optic cable 141 at a modulation device 118 and a beam splitter 123 which passes the entire input beam 117. The input beam 117 is focused by a lens 122. A signal beam 121 is generated within the sample cell 113 and transmitted along the path that the input beam 117 traverses from the beam splitter 123. Upon striking the beam splitter 123, the signal beam 121 is reflected toward an aperture 125. The signal beam 121 can be directed toward the photodetector via fiber optic cable or through air.

Additional examples of optical nonlinear wave mixing instrument designs are further shown in FIGS. 10, 17, 19, 24 and 30 in U.S. Pat. No. 9,244,005B2 which is incorporated by reference.

By employing optical nonlinear wave mixing techniques, the disclosed technology provides optical sensing techniques and devices that are available for chemical or biomedical applications. In conventional technologies, a detection of a target substance are generally based on an imaging technique, for example, magnetic resonance imaging (MRI). The image-based detection technique, however, requires many biomarkers and relatively long time to diagnose a corresponding disease. The disclosed detection technology, which detects a target substance using a chemical/biological reaction occurred in connection with an optical sensing device, provides advantages including increased detection sensitivity and accuracy and fast analysis.

The disclosed optical sensing technology can be implemented to detect various substances for diagnostic applications and food safety applications. For medical diagnostic applications, various target substances are used as a biomarker in performing a diagnostic or screening procedure. In food safety applications, the instrumentation should be portable and robust for field uses such as on a fishery facility away from a testing laboratory facility.

For example, Parkinson's disease (PD) is the second most predominant neurodegenerative disease in the U.S., afflicting 1-2% of the population aged 65 and over. The disease is clinically characterized by the progressive dysfunction of several motor and non-motor neurological functions. A series of studies showed that intercellular accumulation of Lewy bodies (LB), the hallmark of Parkinson's disease, appears 6 years or more before the symptoms emerge. Thus, accurate quantification and detection of LB-related proteins, such as α-synuclein, at a sensitive level is key to pave the way to understanding PD.

α-Synuclein is a 14 kDa, 140-residue neural protein highly expressed in central neurons and localized in presynaptic terminals. The protein is a major component of LBs (aggregated proteins), the hallmark pathology of PD and those with dementia. The mechanisms and inclusion of α-synuclein in LBs do not explain the pathogenesis of the neurodegenerative disease, and it remains unclear whether LBs are a cause or a symptom.

Parkinson's disease was believed to be genetically inherited, since several families with PD history were found to possess a mutation of α-synuclein. Based on this finding, numerous studies developed a hypothesis that both point mutations and multiplications in the α-synuclein gene cause PD. Lee and Trojanowski suggested that β-sheet structure of α-synuclein, readily oligomerized and aggregated, is induced by both pathogenic mutations and elevated levels of α-synuclein. The aggregation of the protein (5-25 µm) is accelerated by various types of post-translational modification, such as Ser-129 phosphorylation, calpain-mediated cleavage, O-glycosylation, tyrosine nitration, methionine oxidation and C-terminal truncation.

Currently, the toxicity of the oligomerized and protofibril intermediate α-synuclein is widely accepted. In addition to the LB hallmark, destruction of dopaminergic neurons are observed in early stages of PD. Conway et al. reported that the formation of oligomerized α-synuclein can be accelerated by dopamine, although the mechanism remains unclear. Südhof et al. suggested that the formation of soluble N-ethylmaleimide sensitive factor attachment protein receptor (SNARE) complex, critical to the vesicle fusion leading to dopamine release, is promoted by α-synuclein binding to a vesicular SNARE protein, synaptobrevin-2. On the other hand, Choi et al. reported that large α-synuclein oligomers inhibit neuronal SNARE-meditated vesicle lipid mixing. Therefore, α-Synuclein can be used as a suspect substance for Parkinson's Disease.

There are other various examples of suspect substances that need to be identified in various applications, including prohibited substances in food industry such as Malachite green (MG) and crystal violet (CV).

Figure 3:
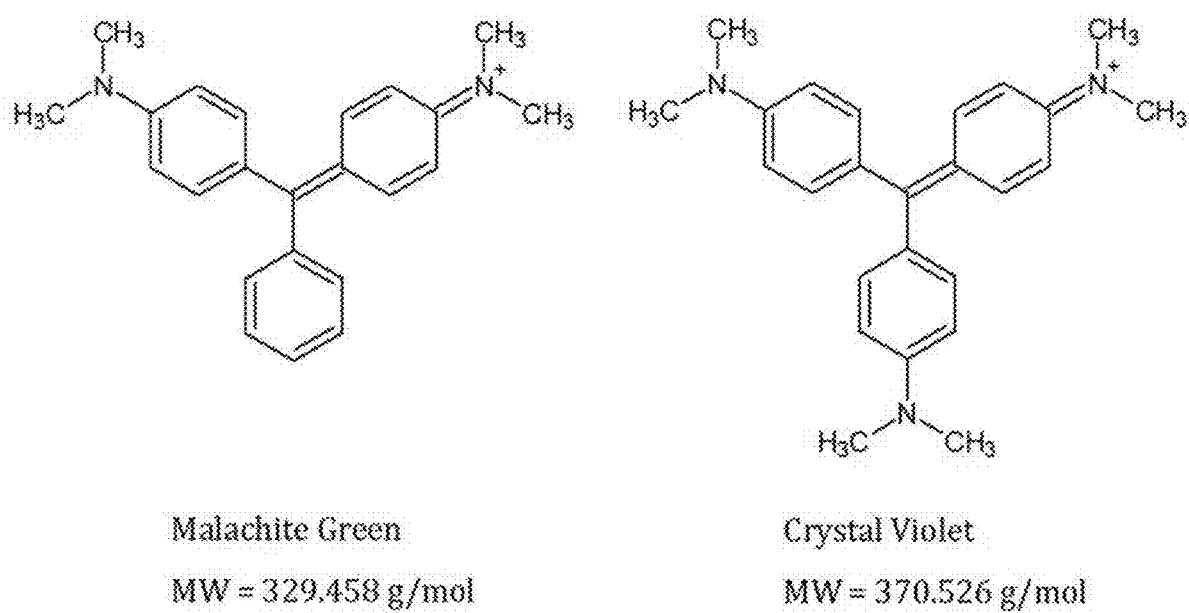
FIG. 3 shows two exemplary suspect substances of Malachite green (MG) and crystal violet (CV).

FIG. 3 shows two exemplary banned substances Malachite green (MG) and crystal violet (CV). MG is a triphenylmethane dye that may be used as a fungicide and paraciticide in aquaculture. However, it is not approved for use as an aquaculture veterinary drug in the United States, Canada or the European Union. Malachite green also has uses as a food coloring agent, as a medical disinfectant and as a dye for textiles. Although a wide range of uses exists, it has also been reported to have toxic effects that increase with concentration, exposure time and temperature. This toxicity may present itself in the form of organ damage and mutagenic, carcinogenic and developmental abnormalities in mammals. Due to reports of this nature, the U.S. Food and Drug Administration (FDA) nominated malachite green as a priority chemical for carcinogenicity testing in 1993.

Crystal violet (CV), which is also shown in FIG. 3, is another triphenylmethane dye used as an anti-microbial and anti-fungal agent for treatment of infections. It has a long history of medical use under the name Gentian Violet, but, like malachite green, crystal violet can be highly toxic and has been shown to enhance tumor growth. Crystal violet also sees use as a DNA stain in gel electrophoresis, which may speak to the carcinogenicity of the compound. As is the case with malachite green, the FDA recognizes crystal violet as unsafe for use as a veterinary drug (21CFR500.29 and 21CFR500.30).

The disclosed technology provides efficient, sensitive, reliable, economic and convenient methods for detecting a target substance in body fluids for diagnosing or screening purposes for example, α-Synuclein, in body fluids for detecting diseases, and for detecting the level of a target substance, e.g., MG or CV, in meats or foods in food safety inspection applications. Depending on the target substance to be detected, the disclosed optical sensing technology will be modified to have different intensity and/or different wavelength to optimize the detection of a particular target substance. In the below, examples of optical sensing techniques are described to detect α-synuclein, MG and CV.

Detection of α-Synuclein

Various body fluids may be analyzed to measure levels of α-synuclein in patients. Cerebrospinal fluid (CSF) analysis based on enzyme-linked immunosorbent assay (ELISA) requires extraction of cerebrospinal fluids and such extraction is invasive and may pose certain risks to patients. Levels of α-synuclein in blood samples may also be tested in order to develop less invasive diagnostic methods for PD. Kasuga et al. reviewed studies of blood samples from a control group and from PD patients to compare α-synuclein levels and concluded that, due to the lack of a sensitive detection and quantification method that can differentiate α-synuclein species (truncated, phosphorylated, monomeric and oligomeric forms), detection of the levels of PD-related proteins in blood samples is difficult to be used as a reliable diagnostic method for PD.

This patent document discloses an optical sensing technology to measure levels of α-synuclein in patients in various body fluids with high detection sensitivity and accuracy to enable early stage PD detection before the PD conditions are developed in advanced stages. The disclosed optical sensing technology can also be used to accurately detect levels of α-synuclein in patients in blood samples that are currently not possible with existing technologies such as methods based on enzyme-linked immunosorbent assay (ELISA). In addition, the present optical sensing technology can be implemented by using widely available inexpensive substances without using specialty substances and complex processes. Furthermore, the present optical sensing technology can be implemented in in relatively compact hardware packaging configurations and potentially portable systems.

The present optical sensing technology for detecting levels of α-synuclein in patients in various body fluids is based on multi-photon nonlinear laser wave-mixing spectroscopy as a novel absorption-based technique that offers excellent detection sensitivity for biomedical applications including early diagnosis and investigation of neurodegenerative diseases. α-Synuclein is linked to Parkinson's disease (PD), and characterization of its oligomers and quantification of the protein may contribute to understanding PD. The laser wave-mixing signal has a quadratic dependence on analyte concentration, and hence, the technique is effective in monitoring small changes in concentration within biofluids. A wide variety of labels can be employed for laser wave-mixing detection due to its ability to detect both chromophores and fluorophores. In the conducted studies, two fluorophores and a chromophore are studied and used as labels for the detection of α-synuclein. Wave mixing detection limits of PD-related protein conjugated with fluorescein isothiocyanate, QSY 35 acetic acid, succinimidyl ester and Chromeo P503 are determined to be $1.4 \times 10^{-13}$ M, $1.4 \times 10^{-10}$ M, and $1.9 \times 10^{-13}$ M, respectively. Based on the laser probe volume used, the corresponding mass detection limits are determined to be $1.1 \times 10^{-23}$ mol, $1.1 \times 10^{-20}$ mol, and $1.5 \times 10^{-23}$ mol, respectively. The conducted studies provide molecular-based separation and quantification of α-synuclein by laser wave mixing coupled with capillary electrophoresis.

The present optical sensing technology can be used to provide a sensitive detection method and an early diagnostic tool for Parkinson's disease and represents a significant different approach to detecting α-synuclein in body fluids in some existing techniques. For example, enzyme-linked immunosorbent assay (ELISA) is commonly used for detecting monomeric and oligomeric forms of α-synuclein in CSF and serum; however, ELISA is usually designed specifically for analyzing a single analyte and cannot be coupled to a separation device. ELISA is a time-consuming assay that requires multiple steps to detect and quantify a target protein. The ELISA well is coated with a target protein-specific antibody that binds to the protein when a sample is introduced. The enzyme-linked antibody may react with an unbound site of the protein. Free antibodies that do not react with the protein are removed by washing. Additionally, ELISA yields inconsistent results for control groups due to background absorption and cross-reactivity interference. The assay may yield false-positive results, i.e., a signal may not be generated by α-Synuclein antigen-antibody reaction or specify monomeric and oligomeric forms.

The wave-mixing detection sensitivity in the disclosed technology is orders of magnitude better than those of conventional absorption techniques, and comparable or better than those of ELISA and fluorescence methods. Laser wave mixing also provides shorter analysis times and better chemical specificity without the use of expensive antibody. Sodium dodecyl sulfate-capillary gel electrophoresis (CGE) or capillary zone electrophoresis (CZE) can distinguish monomeric and oligomeric forms. Unlike laser-induced fluorescence (LIF), laser wave mixing can detect both fluorophores and chromophores. Moreover, the wave-mixing signal is a coherent laser-like beam and it can be detected conveniently with high collection efficiency and high S/N.

Laser Wave Mixing for α-Synuclein Detection

The wave-mixing signal exhibits excellent properties including quadratic dependence on analyte extinction coefficient, i.e., concentration, and cubic dependence on intensity of the excitation laser source. The wave-mixing signal can be described with the following equation.

$$I_3 = \left(\frac{b}{8\pi}\right)^2 / 1^2 / 2\frac{\lambda}{\sin^4(\theta/2)}\left(\frac{dn}{dT}\right)^2 \frac{\alpha^2}{\kappa^2} \tag{1}$$

The intensity of the wave-mixing signal ($I_3$) produced by the probe and pump beams depends on the cross section of the path length of a laser beam (b), intensities of excitation laser source ($I_1$ and $I_2$), the wavelength of the laser source (λ), the angle between the probe and pump beams (θ), a derivative of the refractive index with respect to solvent temperature change (dn/dT), the extinction coefficient (α), and thermal conductivity (k). Equation 1 indicates that the wave-mixing signal has a quadratic dependence on analyte concentration, and hence, it allows more effective measurement of small changes in analyte concentration as compared to conventional absorption and fluorescence methods. Both sensitivity and selectivity levels are enhanced when wave mixing is coupled with CE. Excellent separation resolutions, zeptomole-level sensitivity, fast analysis, and small sample requirements are some of the advantages of wave-mixing CE. Taking advantage of these unique features of laser wave mixing, concentration detection limits of PD-related protein conjugated with fluorescein isothiocyanate, QSY 35 acetic acid, succinimidyl ester and Chromeo P503 are determined to be $1.4 \times 10^{-13}$ M, $1.4 \times 10^{-10}$ M, and $1.9 \times 10^{-13}$ M. Based on the small probe volume (79 pL) used, corresponding mass detection limits of $1.1 \times 10^{13}$ mol, $1.1 \times 10^{-20}$ mol, and $1.5 \times 10^{13}$ mol, are determined.

Materials and Methods

Forward-Scattering Laser Wave-Mixing Experimental Setup

Figure 4:
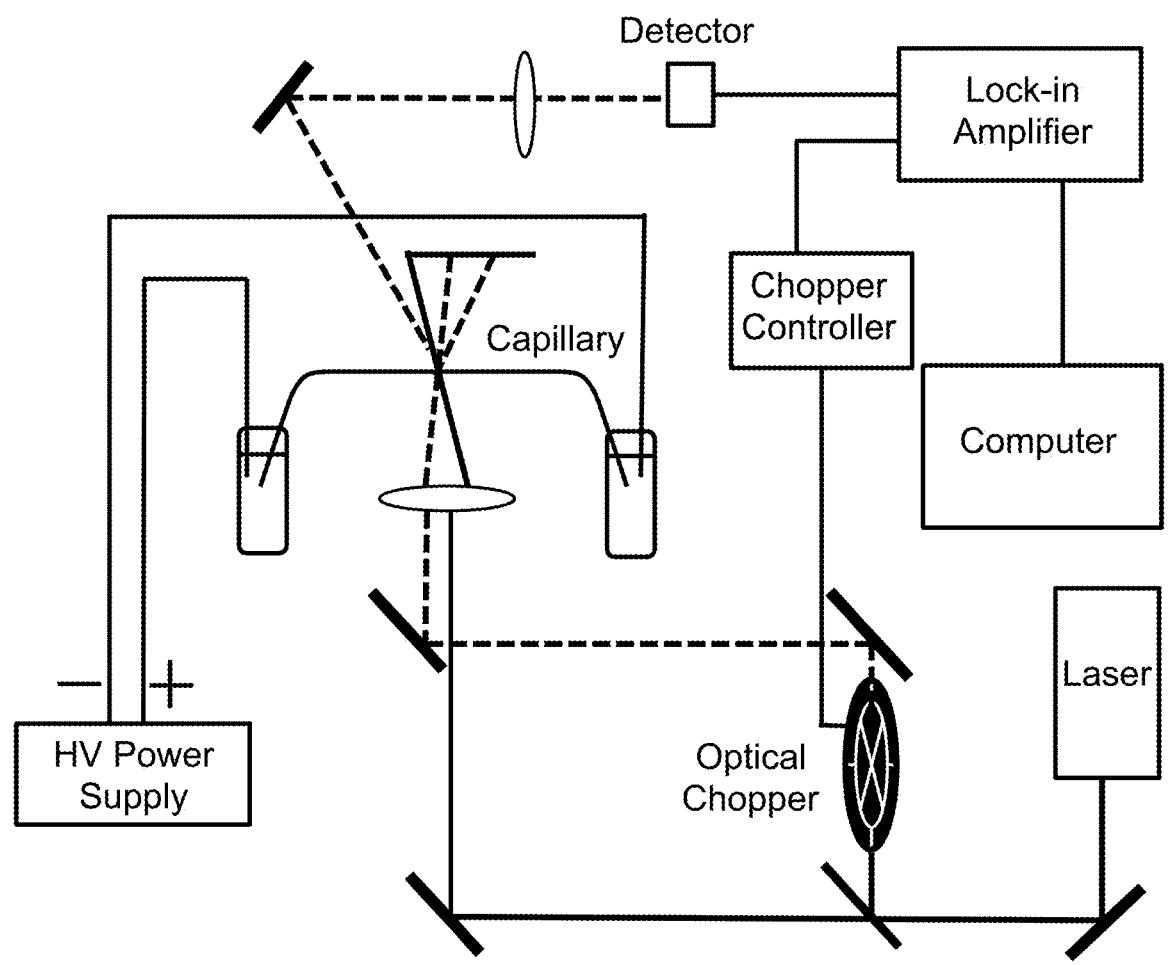
FIG. 4 shows an exemplary wave-mixing scheme coupled with capillary electrophoresis for α-synuclein detection.

FIG. 4 shows a schematic diagram of forward-scattering wave-mixing optical setup interfaced to a CE system. A continuous-wave 488 nm blue laser with adjustable power tuned to 40 mW (Coherent, Santa Clara, Calif.) and a 50 mW 473 nm diode laser (CNI, Changchun, China) are used for visible-wavelength wave-mixing detection. A 266 nm UV pulsed laser (CNI, Changchun, China, 20 mW, 7 kHz) is used for UV wave-mixing detection of α-synuclein. The laser output is first split by a beam splitter (R:T 30:70) to create two input beams. The weaker (reflected) input beam is modulated by an optical chopper (Stanford Research Systems, Sunnyvale, Calif., SR541) at 200 Hz. In FIG. 4, the solid line and the dotted line represent unmodulated and modulated beam, respectively. The two input laser beams travel the same distances and then cross at an angle of 0.95° (488 nm laser) or 1.5° (473 nm laser and 266 nm laser). The excitation lasers yield beam diameters of 1.70 mm (488 nm), 1.20 mm (473 nm) and 1.10 mm (266 nm), and probe volumes of 78 pL (488 nm), 58 pL (473 nm), and 55 pL (266 nm). A 75 µm i.d. fused-silica capillary (Molex, Lisle, Ill.) is used as the analyte cell into which the analyte is loaded by electrokinetic injection. A small portion of the capillary coating is removed by a butane flame so that the input laser beams can propagate through the capillary analyte cell. The wave-mixing signal is collected by a simple photodetector (Thorlabs, Newton, N.J., PDA25K). The optical chopper, the photodetector and the computer are interfaced to a lock-in amplifier (Stanford Research Systems, Sunnyvale, Calif., SR810 DSP).

Chemicals

Solutions used for this study are prepared with distilled water from a compact water distillation system. Borax, Tris base, sodium dodecyl sulfate (SDS), sodium bicarbonate and poly (ethylene glycol) (PEG, 10,000) are purchased from Sigma-Aldrich. Fluorescein isothiocyanate (FITC), CHES, hydrochloric acid, sodium hydroxide, unstained protein ladder, N,N-Dimethylformamide (DMF) and dialysis tubing (MWco 12-14 kDa) are purchased from Thermo Fisher Scientific. The chromophore label, QSY 35 acetic acid, succinimidyl ester is obtained from Life Technologies. The capillary is coated with Ultratrol LN (Target Discovery) by flowing through the solution for 2 to 5 minutes, and a sieving matrix is prepared by flowing PEG in the sample cell. Recombinant α-synuclein, a DNA sequence encoding the human α-synuclein sequence, is expressed in E. coli (rPeptide). Fluorophore protein label, Chromeo™ P503, is purchased from Active Motif. The suggested detection technology can be used either without a label as a label-free detection or with a label. The detection using the labels such as Fluorophore protein label, QSY 35, or Chrome™ P503 is discussed in the descriptions below together with the case not using any label.

Fluorescein Isothiocyanate-Conjugated Protein

Sodium borate reaction buffer (50 mM, pH 8.6) is prepared by dissolving borax in distilled water, and pH is adjusted by using 1.0 M HCl. Proteins are dissolved in the buffer at 2.0-2.2 mg/mL. FITC, a fluorophore label, is dissolved in DMF (10-20 mg/mL) to react with proteins. The mixture of FITC and protein(s) is allowed to proceed for 1 hour in the dark. Dialysis is performed to remove free FITC using regenerated cellulose dialysis tubing (MWco 12,000 kDa-14,000 kDa) and buffer exchange is performed simultaneously to prepare FITC-conjugated protein in Tris-CHES buffer (25 mM) with SDS (0.1%).

Molecular weight and migration time calibration curves are generated by running FITC-conjugated protein ladder that includes seven proteins: lysozyme (14.4 kDa), β-lactoglobulin (18.4 kDa), REase Bsp98I (25.0 kDa), lactate dehydrogenase (35.0 kDa), ovalbumin (45.0 kDa), bovine serum albumin (66.2 kDa), and β-galactosidase (116 kDa). The unstained proteins are present in the solution at various concentration levels (0.10-0.20 mg/mL). The stock solution (150 µL) is aliquoted and dialyzed into conjugation buffer for the protein ladder to react with FITC using the previously stated protocol.

QSY 35 Acetic Acid, Succinimidyl Ester-Conjugated α-Synuclein

Lyophilized α-synuclein is resuspended in 450 µL water to obtain 2.2 mg/mL protein in Tris-HCl and NaCl buffer (pH 7.4). The buffer is replaced with sodium carbonate-sodium bicarbonate reaction buffer (100 mM, pH 8.3) using regenerated cellulose dialysis tubing. α-Synuclein is reacted with QSY 35 in DMF (20 mg/mL) for 1 hour in the dark (1:20). Excess dye is removed by dialysis while carbonate buffer is changed to Tris-CHES (100 mM) with 0.1% SDS.

Chromeo P503-Conjugated Protein

Using an aliquot of 2.2 mg/mL α-Synuclein (100 µL) described above, Chromeo P503 is dissolved in DMF (5.0 mg/mL) and added to the aliquot dropwise to obtain a 1:4 ratio or greater. The solution is gently mixed for 30 minutes until the original color of the dye (blue) changes to red.

Custom-Built Capillary Electrophoresis

Background electrolyte Tris-CHES is prepared by dissolving Tris (1.04 g) and CHES (0.607 g) in distilled water (100 mL) and adjusting pH to 9.0. Sieving matrix is prepared by dissolving PEG (3%) into Tris-CHES buffer (100 mM) with 0.1% high purity electrophoresis-grade sodium dodecyl sulfate (SDS). All the capillary electrophoresis (CE) runs are performed by a custom-built CE system, which uses a fused-silica capillary and a high voltage power supply (Glassman High Voltage, High Bridge, N.J.) that is connected to platinum wires. Voltage is controlled by a custom-built voltage controller. Plastic reservoirs containing running buffer/samples are placed at each end of the capillary.

UV-Visible Absorption Spectra

UV-visible absorption spectra are obtained by a UV-visible spectrophotometer (Agilent, Santa Clara, Calif., 8453) using 1 cm Quartz cuvettes. Absorption spectra are blanked using an appropriate solvent before measuring each analyte.

UV-Visible Analysis of α-Synuclein and Amine-Reactive Labels

Figure 5:
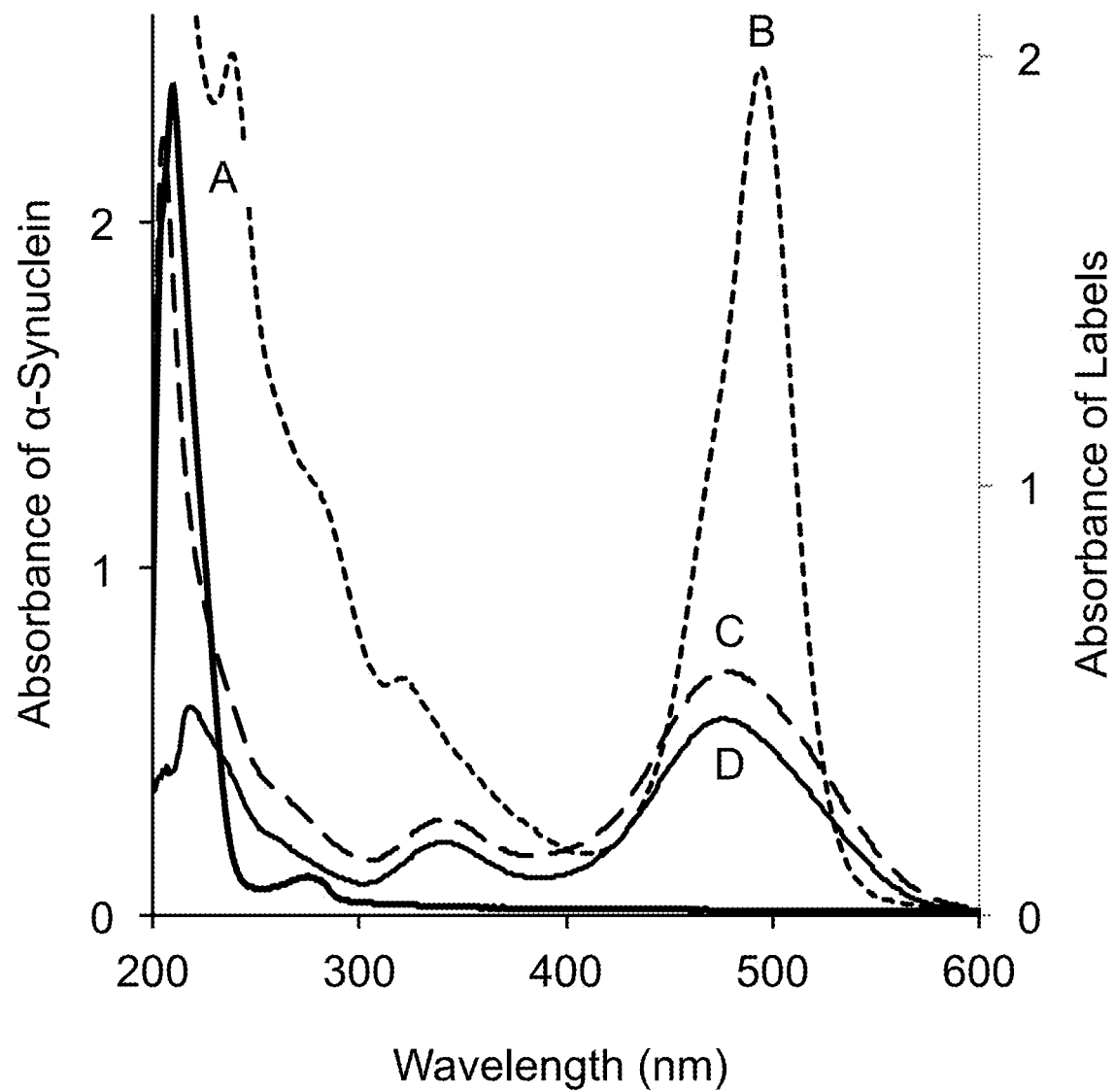
FIG. 5 shows a UV-visible absorption spectra of α-synuclein and labels.

Since laser wave mixing is an absorption-based technique, labels are not required when the analyte absorbs the excitation source. Measuring absorption spectra of analytes allows one to choose an appropriate laser to use in a laser wave-mixing CE setup. FIG. 5 shows UV-visible absorption spectra of α-synuclein and labels used in this study. In FIG. 5, UV-visible absorption spectra of (A) α-synuclein ($1.5 \times 10^{-5}$ M), (B) FITC-conjugated α-synuclein ($7.0 \times 10^{-6}$ M), (C) QSY 35-conjugated α-synuclein ($7.0 \times 10^{-6}$ M), and (D) Chromeo P503-conjugated α-synuclein ($5.6 \times 10^{-6}$ M) is indicated. A, C and D are in carbonate buffer (100 mM, pH 8.3), and B is in borate buffer (50 mM, pH 8.6).

α-Synuclein absorbs UV wavelengths due to aromatic amino acid residues, such as tyrosine and phenylalanine; however, the protein optical absorption is weak at the 266 nm laser excitation wavelength. Nevertheless, laser wave mixing allows label-free detection of the native protein with molar detection limit of 410 µM and mass detection limit of 24 fmol. Label-free wave mixing is still very sensitive at 24 femtomole even when peak absorption is weak at 266 nm UV wavelength, the available laser excitation wavelength, if one desires "label-free" native detection. However, one could also label the analyte and enhance and shift the absorption peak to a visible range and use a visible laser to get a better detection limit if using a labeling extra step is not an issue for the analyte. Many samples encounter labeling issues, e.g., changing the nature of the analytes itself, and hence, a label-free native detection might be more desirable, and wave mixing offers sensitivity levels orders of magnitude better than those available from conventional optical absorption methods. Unlike currently widely used fluorescence-based methods, wave mixing offers excellent detection sensitivity levels for both fluorescing and non-fluorescing analytes. As discussed above, the detection disclosed in this patent document is also can be performed to employ a label. In this case, detection sensitivity can be further enhanced, by conjugating the protein with a label to increase the absorption coefficient. Since every protein possesses N-terminus, and lysine (K) is relatively abundant, amine-reactive dyes are widely used for protein labeling. According to the amino acid sequence of α-synuclein, 16 labeling sites are available for conjugation as shown in FIG. 6; however, due to steric hindrances and the protein conformation, not all the sites are accessible. In FIG. 6, Lysine (K) and N-terminus are amine reactive sites.

FITC is a widely used amine-reactive fluorophore with excitation $\lambda_{max}$ at 495 nm, an excitation coefficient of 70,000 $M^{-1}cm^{-1}$, and emission $\lambda_{max}$ at 525 nm. In this study, 20-mole excess FITC is reacted with the protein for 1 hour before dialysis. QSY 35 is a chromophore label that is used as an acceptor of fluorescence resonance energy transfer (FRET) applications. Its maximum absorbance is at 475 nm with an extinction coefficient of 23,000 $M^{-1}cm^{-1}$ that is suitable for laser wave mixing with an excitation laser source of 488 nm or 473 nm. Chromeo™ 503 displays maximum absorption at 503 nm, and its labeling reaction time is only 30 minutes. The molecular structure of the fluorophore is unclear but Py-1 introduced by Wolfbeis appears to be an identical compound.

Figure 7:
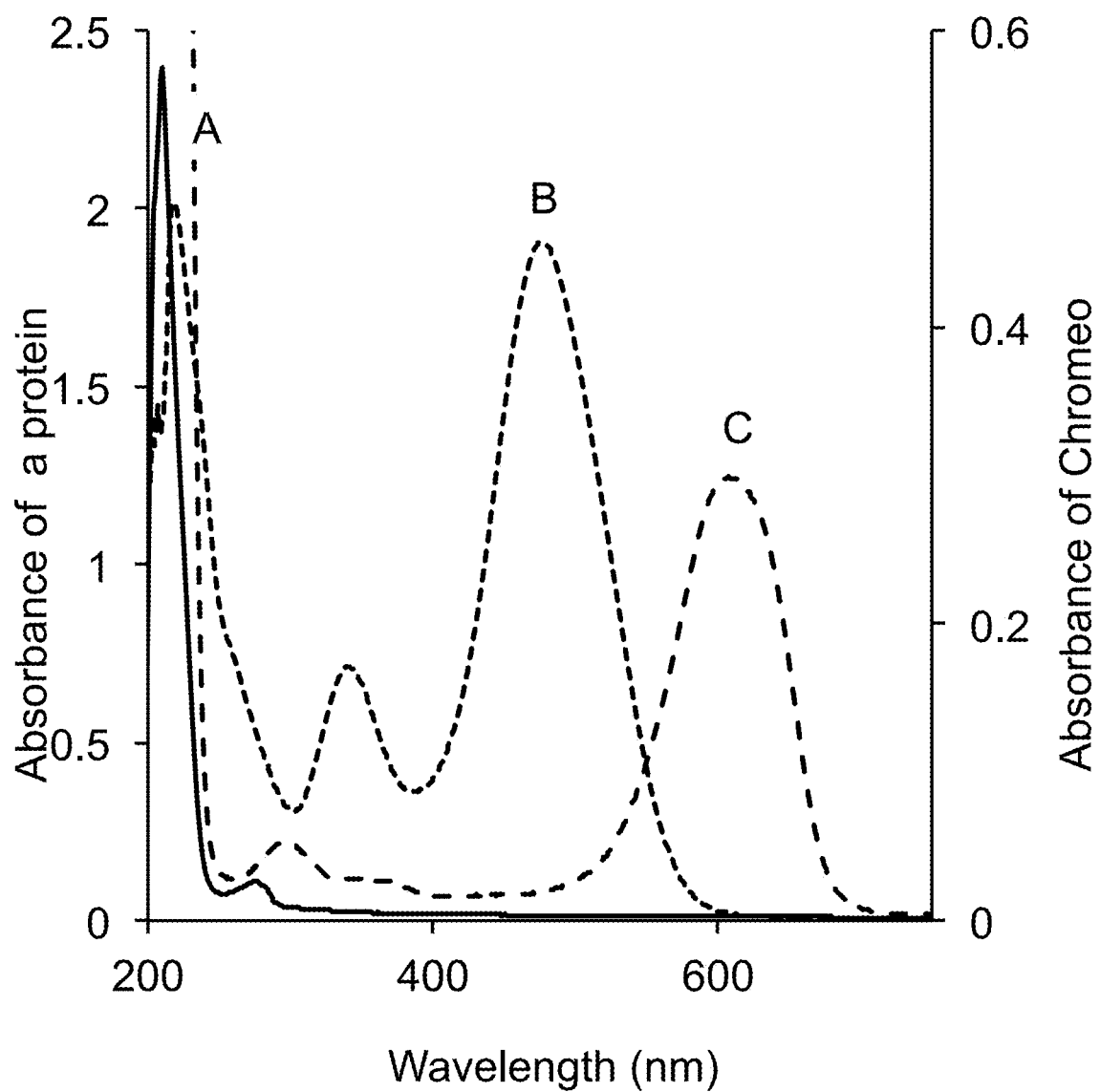
FIG. 7 shows wavelength shift of Chromeo P503 as a fluorophore label.
Figure 8:
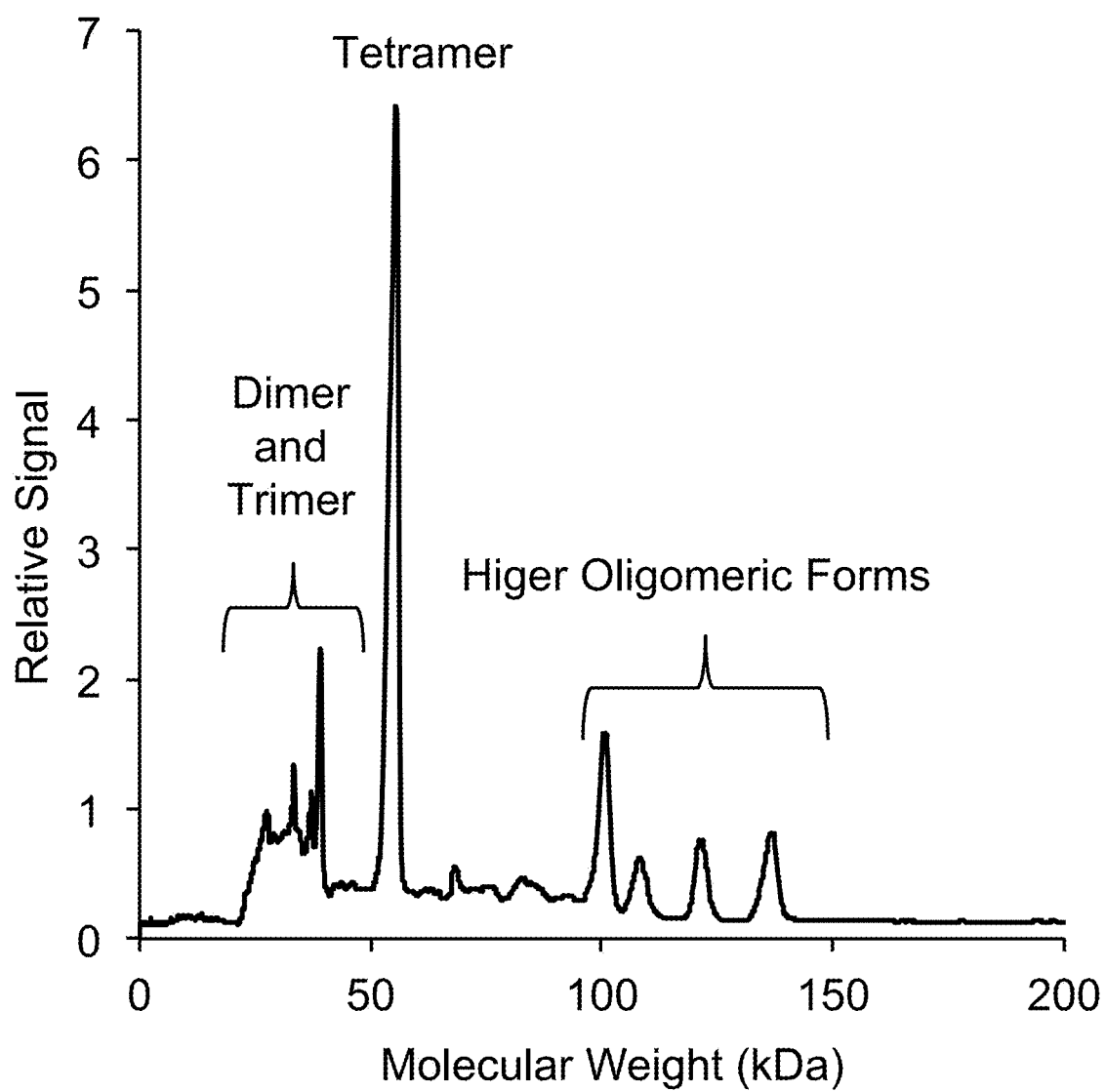
FIG. 8 shows electropherograms of size-based separation of FITC-conjugated α-synuclein.
Figure 9:
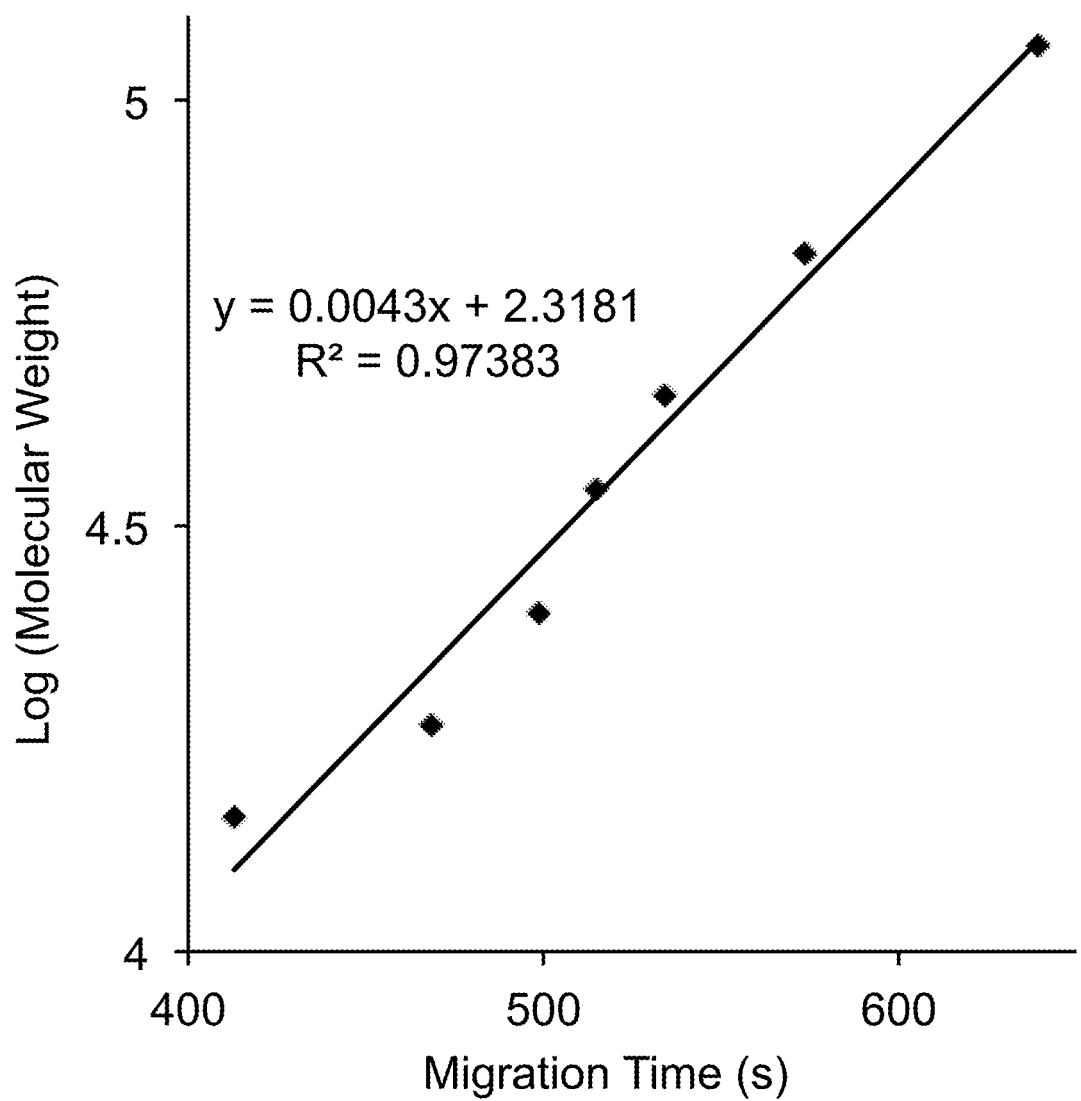
FIG. 9 shows calibration curve created by standard protein ladder for sizing FITC-conjugated α-synuclein.

The unique features of Chromeo P503 as a fluorophore label is shown in FIG. 7. Referring to FIG. 7, wavelength shift is observed for (A) α-synuclein ($1.5\times10^{-5}$ M), (B) Chromeo P503-conjugated α-synuclein ($5.6\times10^{-6}$ M), and (C) Chromeo P503 ($6.4\times10^{-6}$ M). Its absorption peak shifts from 603 nm to 503 nm after conjugation with protein, resulting a color shift from red to blue. That is, conjugation with α-synuclein shifts approximately 100 nm. All solutions are prepared in 100 mM sodium carbonate-sodium bicarbonate buffer (pH 8.3). Chromeo P503-conjugated protein analysis is faster since the reaction time is shorter, and it does not require dialysis when 488 nm laser is used as the excitation source. Extinction coefficient changes from 60,000 $M^{-1}cm^{-1}$ to 24,000 $M^{-1}cm^{-1}$ through the reaction when 4 molar excess label is introduced (manufacturer recommended ratio). There are more un-conjugated labeling sites on the protein as compared to the other two labels with 1:20 (protein:label) reaction ratio. Increasing Chromeo P503 concentration for the reaction can easily enhance the extinction coefficient of the analyte. In addition, Chromeo forms a relatively stable molecule and its stock solution does not deteriorate, so it can be used for several months. Moreover, the dye can be conjugated with a protein without changing the charge of the protein during the process in order to preserve its native form.

α-Synuclein Molecular Weight Determination Using Sieving Capillary Electrophoresis Nonlinear wave mixing, interfaced to capillary gel electrophoresis (CGE), can identify monomer, oligomerized and fibril α-synuclein in their native forms. Detergents have the potential to breakdown physiological assemblies, thus they are not used while performing molecular weight-based separation. FIG. 8 shows an electropherogram of molecular weight-based separation of α-synuclein one can use to identify its oligomeric forms. In FIG. 8, electropherograms of size-based separation of FITC-conjugated α-synuclein ($1.4\times10\text{-}5$ M). The capillary (75 µm i.d., 50 cm) is rinsed with NaOH (0.1 M), water and UltraTrol for 3 minutes followed by running buffer (3% PEG, 100 mM Tris-CHES, and 0.1% SDS). 15.0 kV is applied for each CE run (reverse polarity). The sample is injected electrokinetically for 5 seconds. Wave-mixing signal detected by using a 50 mW 473 nm laser. Molecular weights of the analytes are obtained by running a standard FITC-conjugated protein ladder as shown in FIG. 9. In FIG. 9, calibration curve is created by standard protein ladder for sizing FITC-conjugated α-synuclein. Log of molecular weight versus migration has a linear dependence. The main peaks around 55.3 kDa indicate that the most stable form of α-synuclein is a tetramer with some dimeric (27-39 kDa) and higher oligomeric forms (approximately 100 kDa). The results obtained by this study closely match a study by Bartels et al., wherein the molecular weight of the protein is determined using scanning transmission electron microscopy (STEM) under non-denaturing conditions. They validated their STEM results by sedimentation equilibrium analytical ultracentrifugation (SE-AUC), which is commonly used to establish the oligomeric state of native proteins independent of their conformation. In addition, Bartels et al. developed a non-denaturing method to purify native α-synuclein from RBC, which can be applied to perform analysis with our analytical method. Thus, CE-based laser wave mixing is capable of providing accurate analysis of the native protein conformation and has the potential to help understand the function of α-synuclein for Parkinson's disease.

Pico- and Femto-Molar and Zepto-Mole Detection of α-Synuclein

Figure 10:
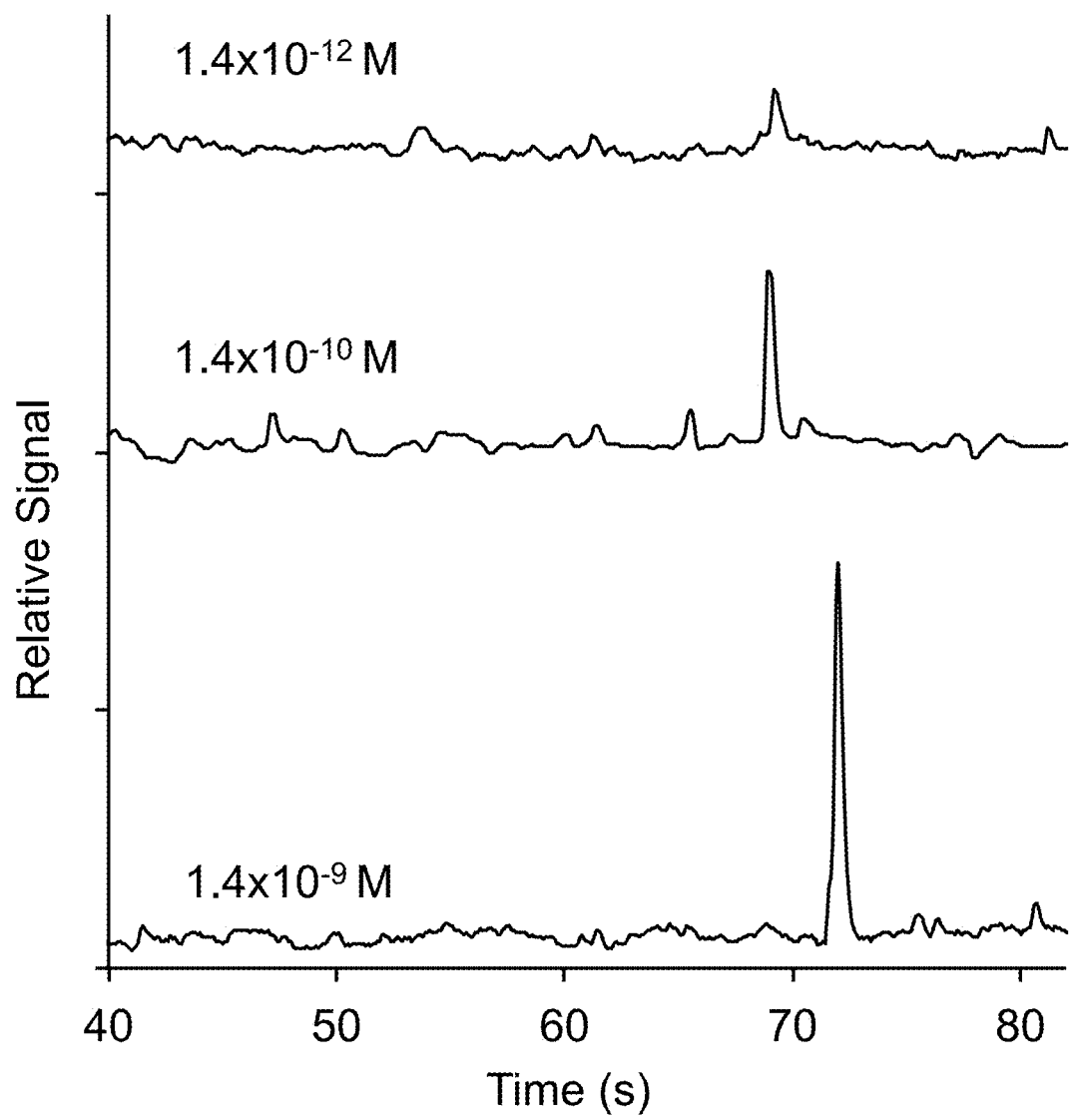
FIG. 10 shows detection limit of FITC-conjugated α-synuclein.
Figure 11:
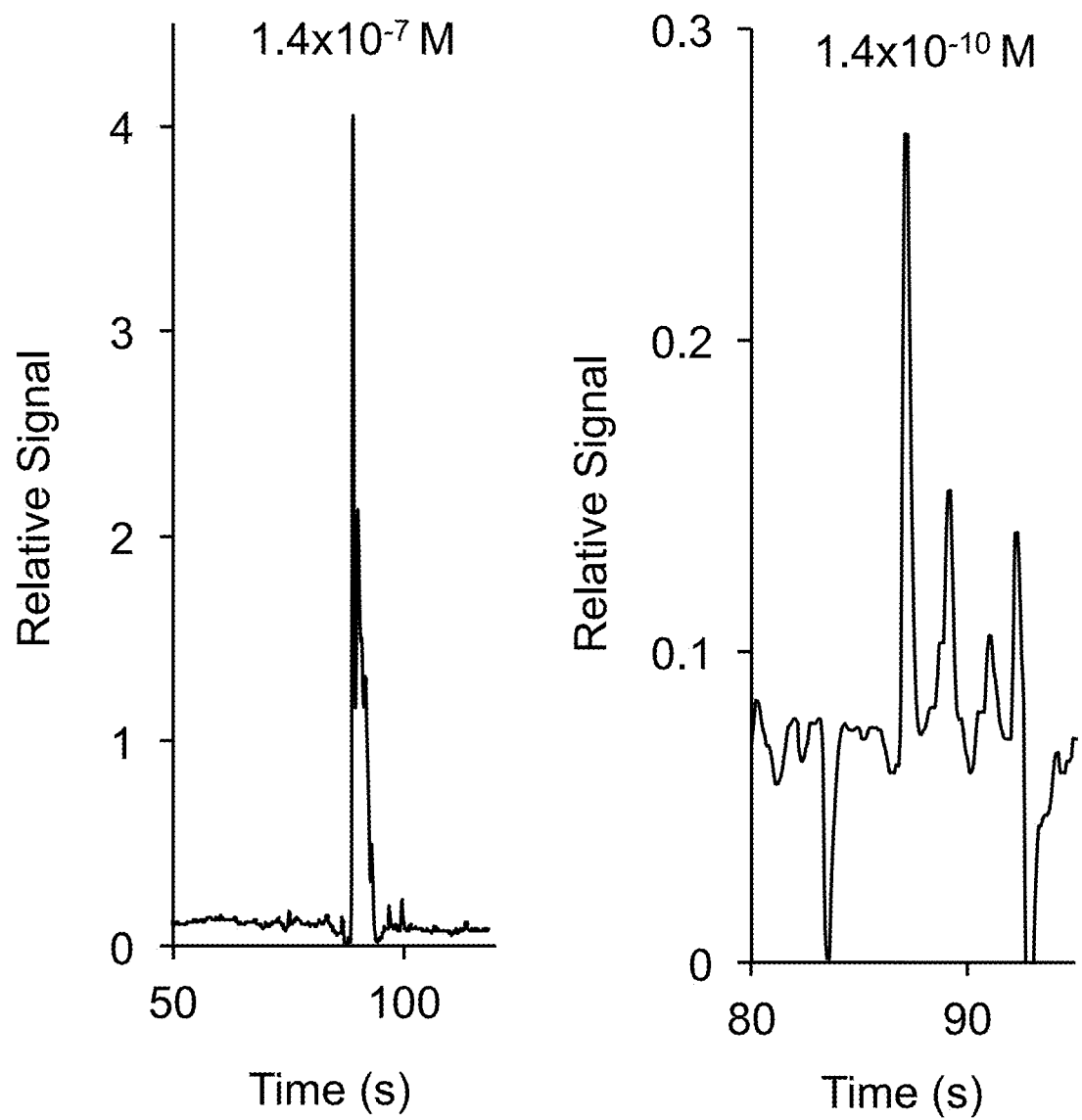
FIG. 11 shows electropherograms of QSY 35-conjugated α-synuclein.
Figure 12:
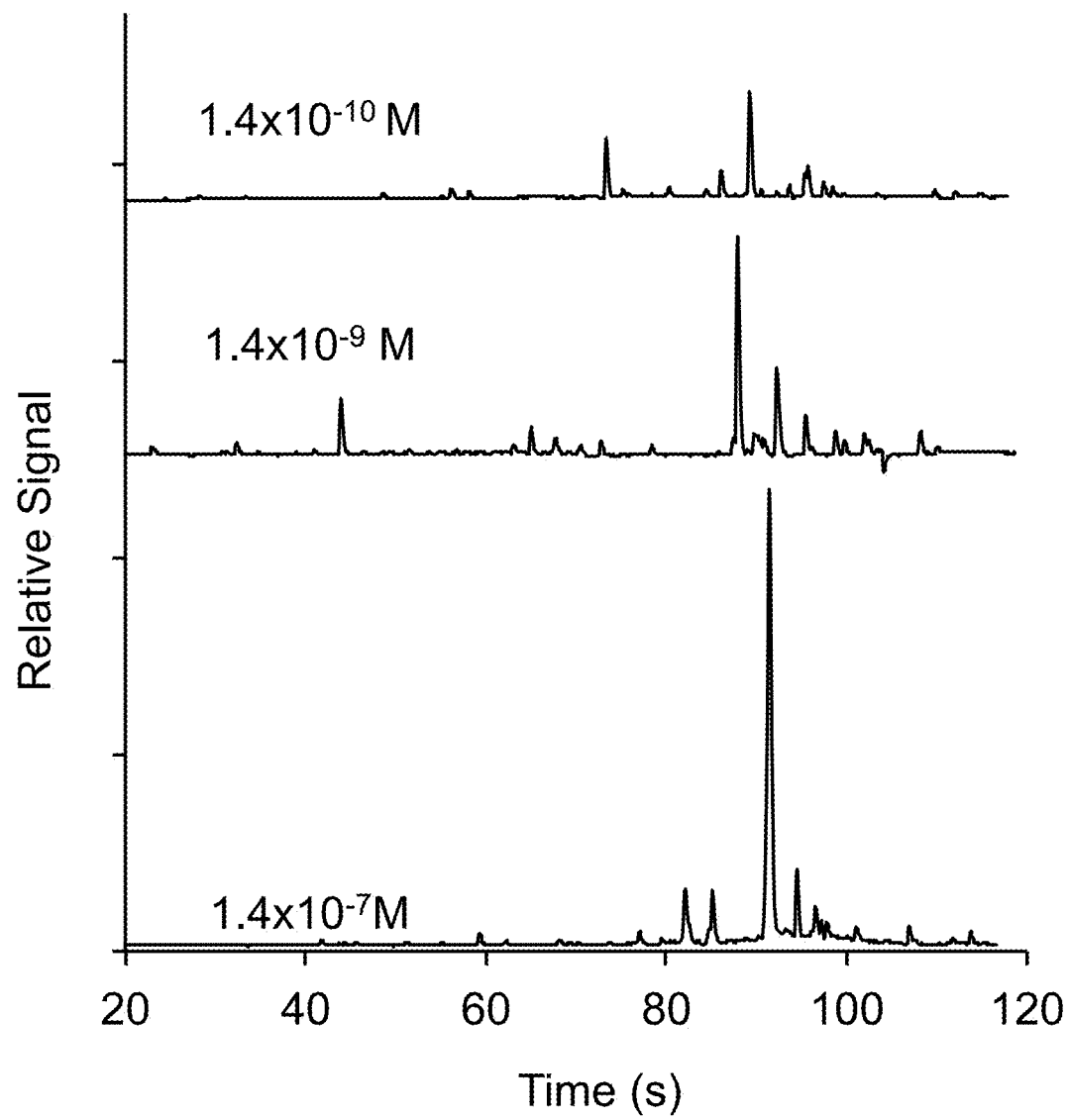
FIG. 12 shows CE-based laser wave mixing detection limit study for Chromeo P503-conjugated α-synuclein.

Laser wave mixing, interfaced to CE, yields excellent detection limits when using label-conjugated α-synuclein. The three types of labels discussed earlier are used in this study. FIGS. 10, 11 and 12 show electropherograms of α-synuclein conjugated with FITC, QSY 35 and Chromeo P503. Each figure is obtained by running CE-based laser wave mixing (488 nm laser) with different concentration levels of labeled proteins. FIG. 10 shows detection limit of FITC-conjugated α-synuclein. Different concentrations, $1.4\times10^{-9}$ M, $1.4\times10^{-10}$ M and $1.4\times10^{-12}$ M, of the protein are detected by CE-based laser wave mixing using a 488 nm laser. The followings are conditions used to obtain results of FIG. 10: Capillary is rinsed with NaOH (0.1 M), water, UltraTrol, and background electrolyte for 3 minutes. Capillary: 75 µm i.d., 30 cm (15 cm effective length). 18.5 kV is applied for each run (reverse polarity). The sample is injected electrokinetically for 20 s.

FIG. 11 shows electropherograms of QSY 35-conjugated α-synuclein ($1.4\times10^{-7}$, and $1.4\times10^{-10}$ M). The followings are conditions used to obtain results of FIG. 11: Capillary is rinsed with NaOH (0.1 M), water, and UltraTrol for 3 minutes followed by running buffer (100 mM, pH 8.6 Tris-CHES). Capillary: 75 µm i.d., 30 cm (15 cm effective length). 18.0 kV is applied for each run (reverse polarity). The sample is injected electrokinetically for 25 s. FIG. 12 shows CE-based laser wave mixing detection limit study for Chromeo P503-conjugated α-synuclein. The followings are conditions used to obtain results of FIG. 12: Proteins are detected at $1.4\times10^{-7}$ M, $1.4\times10^{-9}$ M, and $1.4\times10^{-10}$ M in 25 mM Tris-CHES buffer (pH 8.6). Capillary is rinsed with NaOH (0.1 M), water and UltraTrol for 3 minutes followed by background electrolyte (100 mM, pH 8.6 Tris-CHES). Capillary: 75 µm i.d., 30 cm (15 cm effective length). 18.0 kV is applied for each run (reverse polarity). The sample is injected electrokinetically for 20, 25 and 25 s.

The protein is reacted with FITC and QSY 35 at a ratio of 1 to 20, and Chromeo P503 at 1 to 4, as recommended by the manufacturer for individual labels. Concentration detection limits of $1.4\times10^{-13}$ M (FITC), $1.4\times10^{-10}$ M (QSY 35), and $1.4\times10^{-10}$ M (Chromeo P503) are determined for conjugated α-synuclein as shown in Table 1. Based on the small probe volume used, mass detection limits of $1.1\times10^{13}$ mol (FITC), $1.1\times10^{-20}$ mol (QSY 35), and $1.1\times10^{-20}$ mol (Chromeo P503) are determined for conjugated proteins. This is equivalent to detecting as few as 7 molecules (FITC-labeled) inside the probe volume. FITC-conjugated protein has the highest extinction coefficient at 488 nm, and it reaches the best detection limit by three orders of magnitude as compared to those for QSY 35 and Chromeo P503-conjugated α-synuclein. Migration time for the FITC-conjugated protein is shorter than those of QSY 35 and Chromeo P503 conjugated-protein since higher voltage is applied to the system.

A protein is a relatively large biomolecule that yields a broad peak as compared to that of a small molecule, and multiple peaks are observed in a capillary electrophoresis run. A negatively charged fused-silica capillary wall reacts with multiple charges on protein and causes a high tendency to absorb the protein. To reduce protein-wall interaction in this study, a dynamic coating is applied. The degree of tailing of a peak differs depending on the effectiveness of the wall coating. In addition, there are multiple labeling sites, and individual sites have different reactivity that results in variable labeling and multiple peaks or peak broadening.

Figure 13:
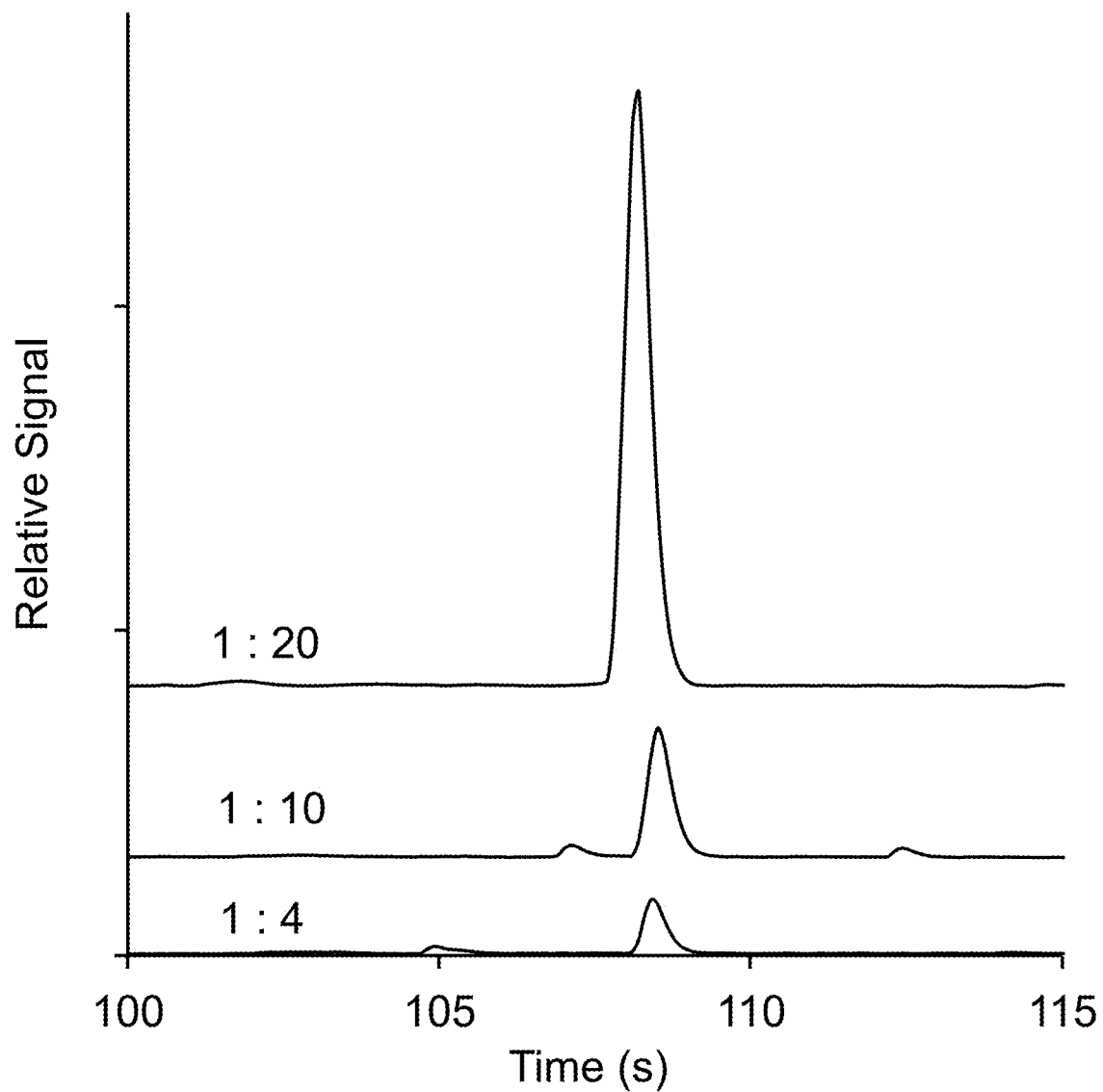
FIG. 13 shows electropherograms of Chromeo P503-conjugated α-synuclein to indicate correlation of reaction ratio and peak height.

By increasing the ratio of Chromeo P503 for the conjugation reaction, the detection limit is improved by three orders of magnitude. FIG. 13 shows electropherograms of Chromeo P503-conjugated α-synuclein to indicate correlation of reaction ratio and peak height. The following conditions are used to obtain results of FIG. 13: Analytes are prepared by using different protein-to-label ratios (1:4, 1:10 and 1:20). Capillary is rinsed with NaOH (0.1 M), water and UltraTrol for 3 minutes followed by running buffer (100 mM, pH 8.6 Tris-CHES). Capillary: 75 μm i.d., 30 cm (15 cm effective length). 18.1 kV applied to each run (reverse polarity). The sample is injected electrokinetically for 15 s. There are 16 available labeling sites for α-synuclein, thus free labels are observed in UV-visible absorption spectra when 20 equivalents of Chromeo P503 are reacted. However, the free label is not observed by CE-based laser wave mixing using a 488 nm laser since free Chromeo P503 scarcely absorbs at that wavelength, shortening sample preparation time by 5 hours as compared to other labels that require dialysis. Minimizing preparation steps results in cleaner optical background and fewer peaks in the electropherogram.

Figure 14:
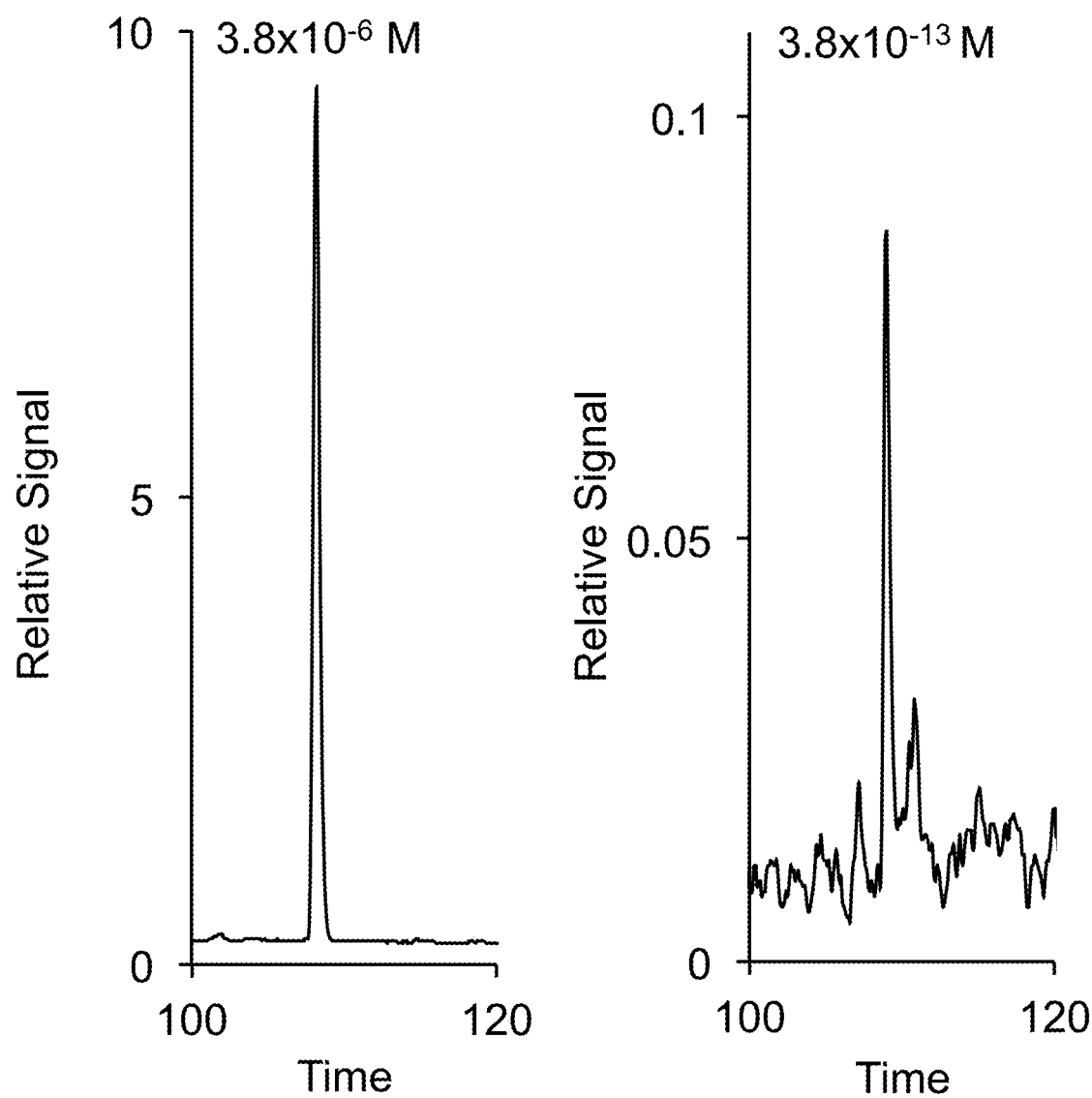
FIG. 14 shows reproducible runs for different concentrations of α-synuclein.

When α-synuclein and Chromeo P503 are reacted with a 1:20 ratio, a concentration detection limit of $1.9 \times 10^{-13}$ M and a mass detection limit of $1.4 \times 10^{-23}$ mol are determined. The mass detection limit corresponds to 9 molecules inside the probe volume. FIG. 14 shows reproducible runs for different concentrations of α-synuclein. In FIG. 14, electropherograms of un-dialyzed Chromeo P503-conjugated α-synuclein (1:20 reaction) are shown. The following conditions are used to obtain results of FIG. 14: Concentrations of the protein are $3.8 \times 10^{-6}$ M and $3.8 \times 10^{-13}$ M in 25 mM Tris-CHES buffer (pH 8.6). The capillary is rinsed with NaOH (0.1 M), water and UltraTrol for 3 minutes followed by running buffer (100 mM, pH 8.6 Tris-CHES). Capillary: 75 μm i.d., 30 cm (15 cm effective length). 18.0 kV is applied for each run (reverse polarity). The sample is injected electrokinetically for 15 and 25 s. With optimal protein-label reaction ratio, the detection limit is further enhanced.

Our wave-mixing setup is not a commercial closed system, thus subtle capillary movement, inconsistent temperature, and other outside elements including dust and noise can affect the laser wave mixing CE signal, especially at zeptomole levels. Noise levels can vary depending on the position of the capillary. To minimize this noise, the capillary is moved horizontally to find the optimal position, which can lead to a migration time shift for CE runs. After multiple runs, two input beams may shift, resulting in a decrease in signal intensity. Since a cooling system is not used for the capillary, inconsistent temperature levels can also affect migration times. The capillary is mounted on a XYZ translational stage and adjusted as needed to maximize the S/N.

TABLE 1

Extinction coefficient and detection limit of labels and label-conjugated proteins.

| Label | Highest Extinction Coefficient ($M^{-1}cm^{-1}$) | Extinction Coefficient at 488 nm with α-Synuclein ($M^{-1}cm^{-1}$) | Detection Limit (M) | Mass Detection Limit (mol) | Number of Molecule |
|---|---|---|---|---|---|
| FITC | 70,000 | 231,000 | $1.4 \times 10^{-13}$ | $1.1 \times 10^{-23}$ | 7 |
| QSY 35 | 23,000 | 78,600 | $1.4 \times 10^{-10}$ | $1.1 \times 10^{-20}$ | 6624 |
| Chromeo P503 1:4 | 24,000 | 78,000 | $1.4 \times 10^{-10}$ | $1.1 \times 10^{-20}$ | 6624 |
| Chromeo P503 1:10 | 24,000 | 133,000 | $1.9 \times 10^{-13}$ | $1.5 \times 10^{-23}$ | 9 |

Quantitative Measurement of α-Synuclein

Figure 15:
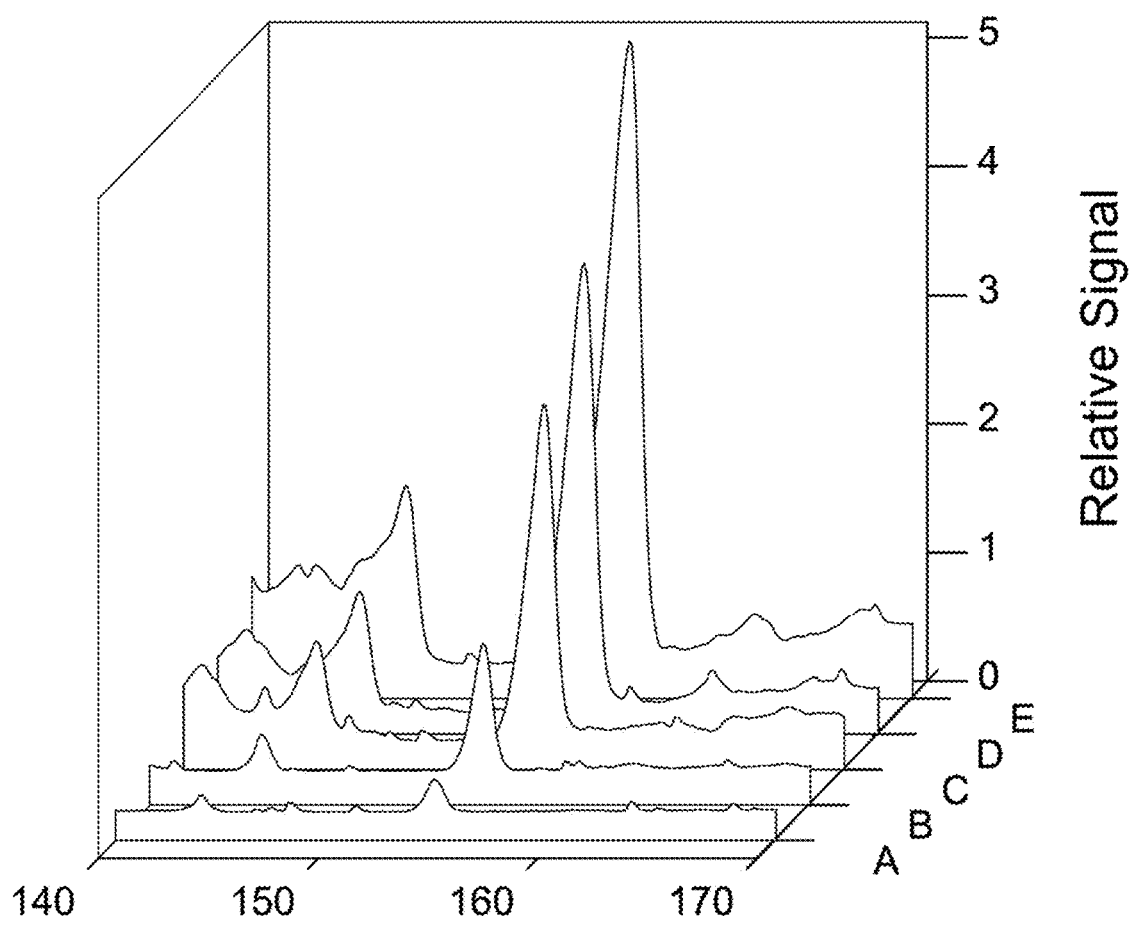
FIG. 15 shows electropherograms of FITC-conjugated α-synuclein detected by laser wave-mixing interfaced with CGE.
Figure 16:
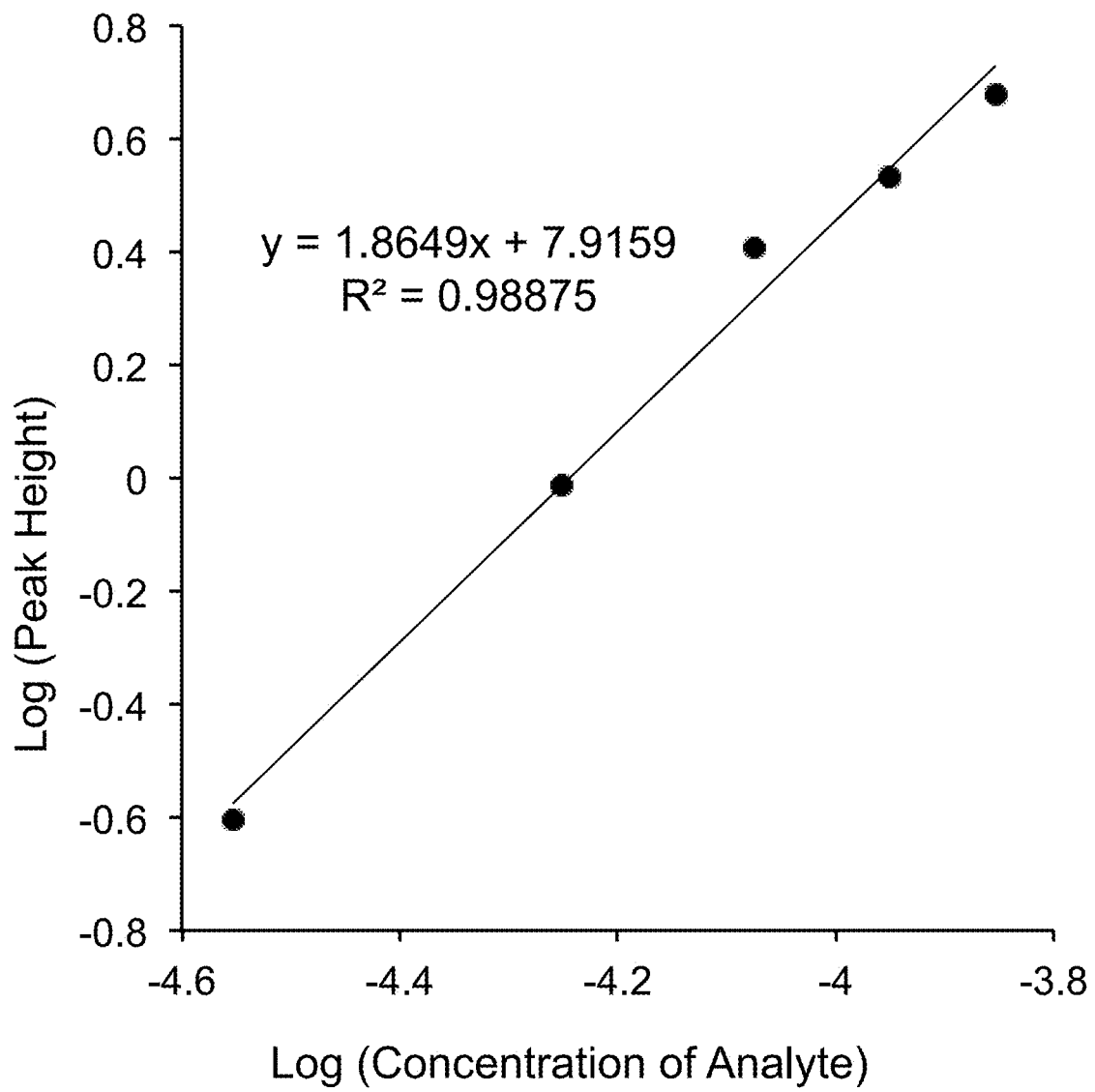
FIG. 16 shows correlations between peak heights and concentrations and a quadratic dependence.

Although laser wave mixing yields strong signals, quantitative measurement of α-synuclein is challenging due to the reasons mentioned in the previous section. FIG. 15 shows electropherograms of FITC-conjugated α-synuclein detected by laser wave-mixing interfaced with CGE. In FIG. 15, proteins are detected at different concentrations: (A) 28 μM, (B) 56 μM, (C) 84 μM, (D) 112 μM, and (E) 140 μM in 25 mM Tris-CHES buffer (pH 8.6). To obtain results of FIG. 15, the following conditions are set: Capillary is rinsed with NaOH (0.1 M), water and UltraTrol, and running buffer (3% PEG, 100 mM Tris-CHES, and 0.1% SDS) for 3 minutes. Capillary: 75 μm i.d., 30 cm (15 cm effective length). 15.0 kV is applied for each run (reverse polarity). The sample is injected electrokinetically for 5 s and detected by a 50 mW 473 nm laser. The capillary is filled with 3% PEG and powered by 15 kV to obtain molecular weight-based separation. The laser wave-mixing signal has a quadratic dependence on analyte concentration, and hence, it allows more reliable monitoring of small changes in analyte concentration. FIG. 16 shows correlations between peak heights and concentrations and a quadratic dependence. The protein is detected at the following concentration levels: 28, 56, 84, 112 and 140 μM. Peak heights and areas are measured using Origin 8.5. Peak area vs. concentration plot also shows a nearly quadratic dependence (slope of 1.87). The slope is not exactly 2.0 (theoretical value) for peak heights and peak areas due to some background noise and exterior influences.

Laser wave mixing, interfaced to CE, offers high S/N and yields reproducible CE runs, while ELISA struggles with background control absorption and cross-reactivity interferences that result in false results. Moreover, CE-based laser wave mixing is much faster than ELISA and SDS-PAGE. Thus, this nonlinear absorption-based wave-mixing detection method is promising for fast and reliable analyses of clinical samples.

Nonlinear absorption-based laser wave mixing provides ultrasensitive detection for FITC, QSY 35 and Chromeo P503-conjugated protein related to Parkinson's disease. FITC and Chromeo P503-conjugated analytes yield the best detection limits. The wave-mixing signal is a coherent laser-like beam that can be collected with excellent efficiency and high signal-to-noise ratios. Laser wave mixing is convenient and faster than SDS-PAGE and ELISA in determining molecular weight of a protein for the purpose of investigating oligomeric forms. While this paper focuses on separation of multi-forms of α-synuclein, other studies show that the aggregation of the protein is accelerated by post-translational modification such as Ser-129 phosphorylation. Laser wave-mixing detection coupled with CE could also separate and detect phosphorylated α-synuclein by modifying CE matrix and additives since it can separate peptides with a one-amino-acid difference and even isomers. Potential applications include sensitive, reliable, fast and convenient detection of α-synuclein for early diagnosis of Parkinson's using a few drops of blood sample.

According to implementations of the disclosed technology, several advantages can be achieved. For example, the detection sensitivity can be significantly enhanced. The disclosed laser wave mixing offers much better detection sensitivity levels that allow, for the first time, potential diagnostics of early-stage Parkinson's and other neurodegenerative disease. Ultrasensitive detection sensitivity levels could also allow the use of CSF and even blood samples instead of only the brain fluid. Existing MM and other imaging-based diagnostic methods cannot detect these biomarkers until it is too late and the symptoms are already apparent. Some existing chemical-based detection methods lack sensitivity levels for early-stage diagnostics. Also, the detection can be done faster. The conventional methods require time-consuming sample preparation steps and/or expensive protocols using proprietary tags and labels, e.g., ELIZA-based methods and all methods based on fluorescence detection methods that are widely used. Also, the detection can be done easily by providing the portability. The disclosed laser wave-mixing detectors coupled with nanofluidics and microfluidics offer excellent chemical specificity and detection sensitivity levels using much more compact, and hence, portable designs, as compared to benchtop full-size instruments currently used. Hence it offers potential use at home and in the field, for the first time, e.g., doctor's office, bed side, etc. Also, when coupled to nanofluidics and microfluidics, laser wave mixing offers excellent chemical specificity levels that allow separation of biomarkers at high resolution. Also, the disclosed laser wave mixing does not require special proprietary commercial tags and labels. One can use commonly available fluorophore labels. Laser wave mixing also allows the use of less expensive and more commonly available chromophore labels instead of more expensive fluorophore labels. The disclosed laser wave mixing can be performed either with a label or without a label. When the disclosed laser wave mixing is performed without any label, biomarkers can be detected label-free in their native form. When the disclosed laser wave mixing is performed with a label, the sensitivity and the accuracy of the detection can be further increased.

Detection of Malachite Green (MG) and Crystal Violet (CV)

This patent document discloses optical sensing systems and methods for using optical nonlinear wave mixing for label-free and tag-free enhanced detection sensitivity and accuracy in detecting a low concentration level of a suspect substance such as Malachite Green and Crystal Violet. The disclosed optical sensing systems and methods can be implemented as necessary to allow the detection for a particular suspect substance only or the detection for multiple suspect substance at one time. For example, some implementations of the disclosed technology enable to detect either Malachite Green or Crystal Violet, while other implementations enable to simultaneously detect both Malachite Green and Crystal Violet. The optical devices described in this document uses a portable compact design and can be packaged as portable systems to allow users to carry them into fisheries, factories, plants, farms and other facilities. This portable compact design allows to perform on-site optical testing of a suspect substance in the field for real-time dynamic measurements of chemical agents in fish, meats and foods instead of having to collect the samples and taking the samples back to a laboratory for analysis as done by currently available analytical methods. Laser wave mixing offers real-time dynamic measurements with high spatial resolution (physical locations) instead of collected samples from different spots at a fishery and then analyzing the samples at a laboratory later with some risk of some sample degradation and contamination.

Due to the health risks and the potential for illegal use in trace amounts, for malachite green and crystal violet, a very sensitive analytical detection method is needed to identify trace quantities in an aquaculture setting. Both malachite green and crystal violet are readily absorbed into fish tissues, which may then be ingested by consumers. Absorbed malachite green and crystal violet may also be metabolized to leuco malachite green (LMG) and leuco crystal violet (LCV). Current detection methods often involve expensive, complicated techniques such as mass spectrometry to obtain low detection limits; while many of the simpler methods are not capable of measuring below nanomolar concentration levels. This leaves a need for simple, yet sensitive, detection methods that can be field-deployed to confirm the presence of these hazards in water supplies or animal tissues. The method of detection described in this work utilizes absorptivity, molecular weight and charge to identify these drugs at sub-nanomolar concentrations by laser wave mixing coupled with capillary electrophoresis (CE). In addition to analysis of water samples, our separation and detection methods may be paired with existing sample extraction techniques to analyze residues present in tissues.

An ultrasensitive label-free antibody-free detection method for malachite green and crystal violet is presented using nonlinear laser wave-mixing spectroscopy and capillary zone electrophoresis. Wave-mixing spectroscopy provides a sensitive absorption-based detection method for trace analytes. This is accomplished by forming dynamic gratings within a sample cell, which diffracts light to create a coherent laser-like signal beam with high optical efficiency and high signal-to-noise ratio. A cubic dependence on laser power and square dependence on analyte concentration make wave mixing sensitive enough to detect molecules in their native form without the use of fluorescent labels for signal enhancement. A 532 nm laser and a 635 nm laser were used for malachite green and crystal violet sample excitation. The use of two lasers of different wavelengths allows the method to simultaneously detect both analytes. Selectivity is obtained through the capillary zone electrophoresis separation, which results in characteristic migration times.

Measurement in capillary zone electrophoresis resulted in a limit of detection of $6.9 \times 10^{-10}$ M ($2.5 \times 10^{-19}$ mol) for crystal violet and $8.3 \times 10^{-11}$ M ($3.0 \times 10^{-20}$ mol) for malachite green at S/N of 2.

Laser wave mixing is a powerful spectroscopic method that produces a signal through the formation of a thermal grating at the intersection point of two input laser beams (pump and pump/probe) passing through an absorbing analyte. The angle of the input beams determines the angle of the two signal beams, which allows a predictable location for collection by a photodetector. Because the input beams are derived from one laser source split by a 70:30 beam splitter, the signal beam produced from the pump/probe beam is stronger than the one produced by the pump beam. This signal has a square dependence on analyte absorptivity or concentration and a cubic dependence on laser power. These properties allow the method to use low-power laser efficiently to excite molecules even if they do not have a large extinction coefficient. This allows a very dilute sample to produce a strong signal as described below.

$$I_s = \left(\frac{b}{8\pi}\right)^2 I_2^2 I_1 \frac{\lambda_e}{\sin^4(\theta/2)} \left(\frac{dn}{dt}\right)^2 \frac{\alpha^2}{\kappa^2} \quad (2)$$

In Equation 2, signal intensity is represented by $I_s$, and the pump beam intensities are $I_1$ and $I_2$. b is the optical path length of the sample cell, $\lambda_e$ is the excitation wavelength, $\theta$ is the angle between the pump beams, and dn/dt is the change in the refractive index with respect to temperature. $\alpha$ is the absorptivity/extinction coefficient of the analyte, and $\kappa$ is the solvent thermal conductivity.

Figure 17:
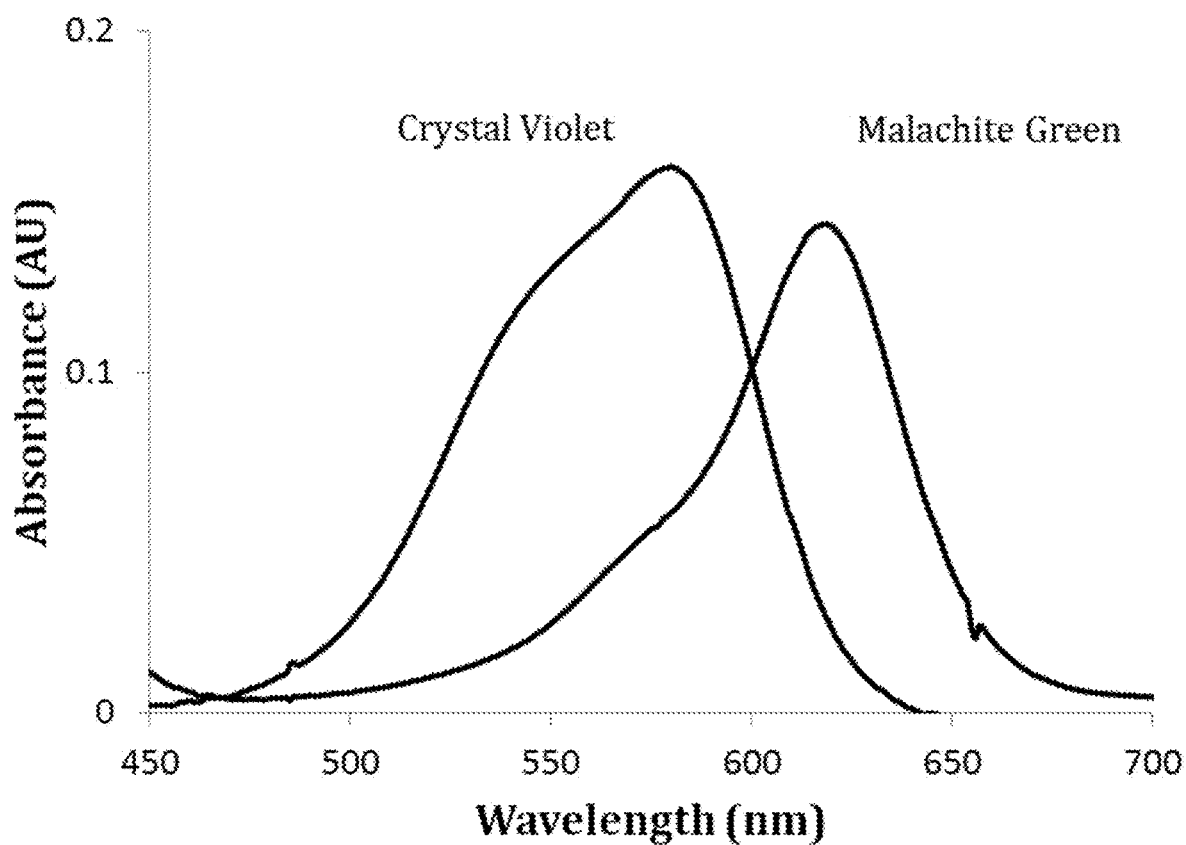
FIG. 17 shows an UV-visible spectra of malachite green (1.0 µM) and crystal violet (1.0 µM).

Given that malachite green and crystal violet both yield strong optical absorption in the visible range, as shown in FIG. 17, visible laser wavelengths closest to the peak absorption wavelengths will yield the strongest wave-mixing signals. For crystal violet, peak absorption was determined to be at 580 nm with an extinction coefficient of approximately 160,000 cm$^{-1}$ M$^{-1}$. Malachite green peak absorption was determined to be at 618 nm with an extinction coefficient of approximately 140,000 cm$^{-1}$ M$^{-1}$. The 532 nm laser excitation wavelength falls at 61% of crystal violet $\lambda_{max}$ and the 635 nm laser excitation wavelength at 68% of malachite green $\lambda_{max}$. The broad absorption peak for malachite green actually allows a small amount of absorption from the 532 nm Nd:YAG laser, as well as the 635 nm diode laser used in this work. However, the same is not true for crystal violet, which does not show significant absorption near 635 nm. Furthermore, as the leuco-forms of malachite green and crystal violet (LMG and LCV) are colorless, they cannot be detected directly by the lasers used in our system. However, given the significance of these derivatives in tissue sample analysis, extensive research on sample preparation has identified oxidation reactions that convert the leuco-forms back to the original colored compounds malachite green and crystal violet. LMG and LCV samples collected and oxidized in this manner may be analyzed concurrently with malachite green and crystal violet as aggregate peaks.

Chemicals

Malachite green chloride and crystal violet were purchased from Sigma Aldrich. Ultratrol LN was purchased from Target Discoveries. All other chemicals were of analytical grade. Deionized water was distilled prior to use in capillary electrophoresis buffer solutions. Buffers were filtered through 0.2 µm syringe filters prior to use as a sample diluent or in the capillary electrophoresis system.

Laser Wave Mixing System

Figure 18:
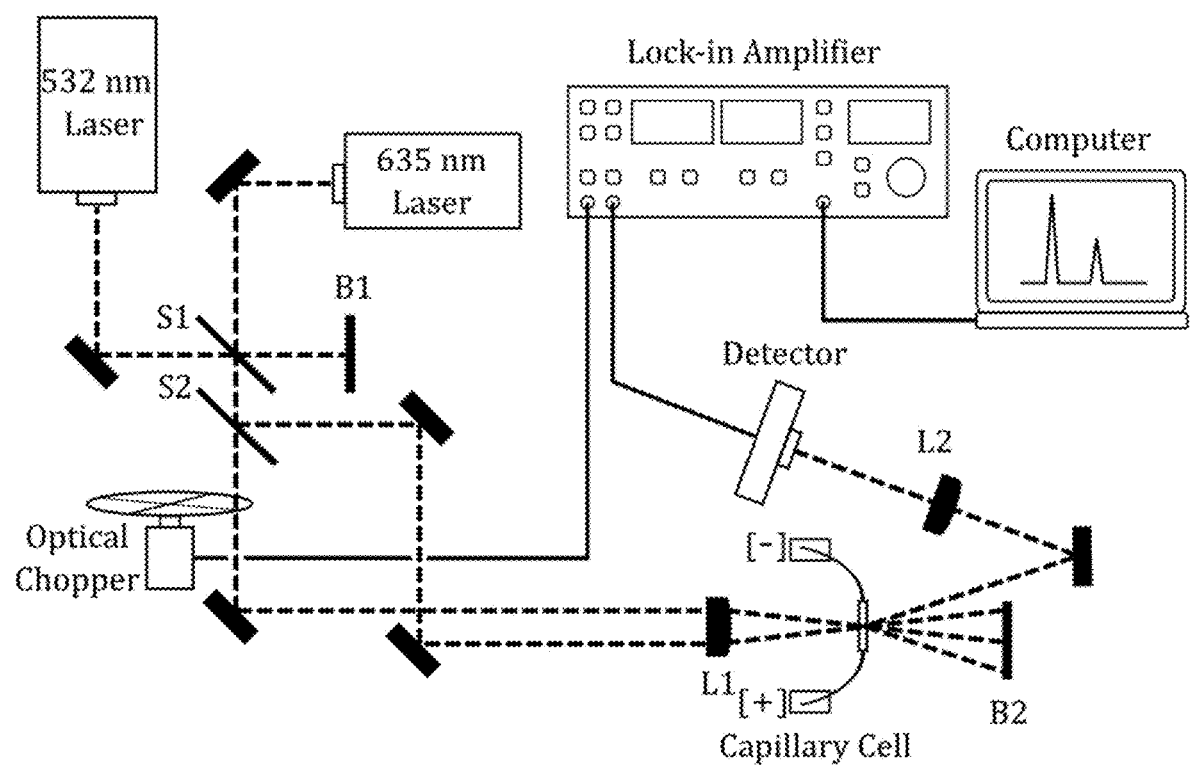
FIG. 18 shows an exemplary experimental setup for wave-mixing detection of malachite green and crystal violet.
Figure 19:
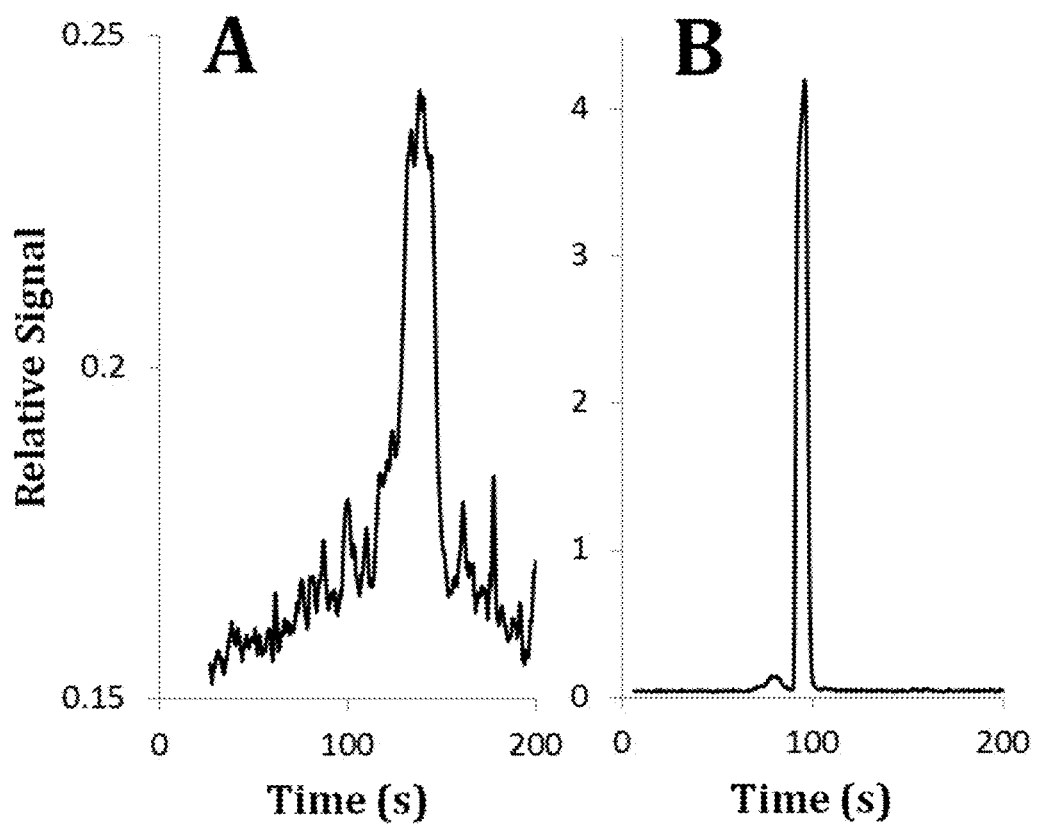
FIGS. 19A and 19B show electropherograms for 1×10-4 M crystal violet (CV) prepared in 50 mM aqueous citric acid solution only and 50 mM aqueous citric acid diluted with acetonitrile, respectively.

A wave-mixing optical configuration described in our previous work was utilized for analyte detection. A 200 mW 532 nm frequency-doubled Nd-YAG laser (CNI, MGL-FN-523-200 mW) and a 100 mW 635 nm diode laser (Laserglow Technologies, LRD-0635-TSR-00100-10) were positioned so that both beams converged at a 90-degree angle on a single 70/30 (70% transmitted, 30% reflected) beam splitter, as shown in FIG. 18. The 532 nm laser and the 635 nm laser were used to excite crystal violet and malachite green respectively, since they are compact, portable, rugged, power-efficient, solid-state lasers that are suitable for field use, although their wavelengths are not exactly at the absorption peaks as shown in FIG. 17. Lase wave mixing offers excellent detection sensitivity levels, and hence, the sensitivity level is still excellent even when using off-resonant wavelengths to excite the analytes. Thus, the excitation wavelength does not have to be at the peak absorption wavelength. In addition, these off-resonant wavelengths were selected to use dual-wavelength cross verification and enhance chemical selectivity and confirmation, i.e., each wavelength of 532 nm and 635 nm could excite both CV and MG analytes and the resulting absorption ratios at the two wavelengths can be used to further confirm both CV and MG analytes. This allowed approximately 70% of the 635 nm beam and 30% of the 532 nm beam to pass through the optical setup. Taking into account additional losses due to mirrors used to align the beams and spatial filters, the final effective laser powers were 65 mW and 40 mW, respectively. After the initial power reduction, the two beams were directed to a second beam splitter (70/30 R/T) to create two pairs of overlapping beams, with the weak-side beams passing through an optical chopper (SRS, SR540). These beams were then redirected by three mirrors to allow parallel paths into a 10 cm focusing lens. A polyimide coated silica capillary with 1 cm of its coating removed was placed at the focal point to allow the two pairs of beams to converge at the detection window. A spatial filter was placed behind the capillary to isolate only the strong-side signal beams from the remaining three pairs of beams. These overlapping signal beams were then reflected off of a mirror and through another 10 cm focusing lens. A photodetector (Thorlabs, PDA36A) was used to collect the signal, which was processed by a lock-in amplifier (SRS, SR810 DSP) and then digitized using our custom-built AIDA data acquisition software.

Capillary Electrophoresis System

The custom-built capillary electrophoresis system utilized a 30 kV power supply (Glassman PS/MJ30P0400-11) with a custom-built control system to apply current across the system. The suggested capillary electrophoresis system is more compact and suitable for interfacing it to the compact laser wave-mixing detector. Polyimide coated fused silica capillaries including 360 µm o.d., 100 µm i.d., 35 cm (17 cm effective) and 360 µm o.d., 75 µm i.d., 40 cm (20 cm effective), were used for various experiments. Platinum electrodes were placed in glass sample vials at both end of a capillary, while system voltage and current were monitored by a multimeter and our AIDA data acquisition software. Ammonium acetate buffer (50 mM, pH 5.1) was prepared in distilled deionized water. Buffer solutions of 50 mM (pH 2.2) or 0.5 mM citric acid (pH 3.5) were prepared in distilled deionized water and then diluted 2:1 with acetonitrile similarly to methods previously reported. MG and CV samples were prepared in 0.5 mM citric acid and acetonitrile (1:2), 50 mM citric acid and acetonitrile (1:2) or 50 mM ammonium acetate. Electrokinetic sample injection (+20 kV) was used to introduce our analytes. Prior to use, capillaries were treated with 0.1 N NaOH for 10 minutes at 5 µL/min using a peristaltic pump, followed by priming with run buffer for 1 minute at the same flow rate. For capillary coating, Ultratrol LN capillary dynamic coating polymer (Target Discoveries) was flowed into the capillary at 5 µL/min between the standard 0.1 N NaOH and run buffer treatment steps. Between sample runs, capillaries were flushed with 0.1 N NaOH and run buffer for 1 minute at 5 µL/min.

Background Electrolytes

Initial attempts to detect MG and CV in the capillary electrophoresis mode were made using an aqueous 50 mM ammonium acetate buffer (pH 5.1). This buffer was chosen due to its acidic pH and the successful application of a similar solution. However, when used as the sample solvent and background electrolyte in the capillary electrophoresis system, the current was found to be excessively high (>240 µA) at 20 kV applied voltage. Through multiple sample injections with this buffer, only two successful runs were recorded without loss of system conductivity. Despite the use of long injection times, signal response was found to be relatively poor in the 50 mM ammonium acetate system. The weak signal, combined with the frequent boiling of the buffer due to high current, ultimately led to a change in CE run buffer.

While a reduction in ammonium acetate concentration would have reduced system current to more manageable levels, the signal would have still been weak and the sensitivity for MG and CV detection would have been limited. For this reason, another acidic run buffer was formulated using 50 mM citric acid. This system was chosen for its reported success as a capillary electrophoresis buffer in a 2007 work. Initial testing of this 50 mM citric acid solution in the CE system showed a significant reduction in current to an average of 70 µA with a constant +20 kV applied voltage. This current decrease vs. ammonium acetate is due to a change in conductivity resulting from the higher molecular weight of citric acid. Although a more stable CE system was possible with this buffer, the wave-mixing signal response was found to be even lower than with the ammonium acetate buffer. The electropherogram peaks were also very broad and non-Gaussian in shape, as shown in FIGS. 19A and 19B. $1 \times 10^{-4}$ M crystal violet (CV) is used to obtain results of FIGS. 19A and 19B and the capillary electrophoresis has the following parameters: 20 kV, 75 µm i.d., 360 µm o.d., 40 cm capillary (20 cm effective length), 30 s (A) and 5 s (B) electrokinetic injections. This observation suggested poor analyte solubility in a purely aqueous citric acid solution, which may have resulted in capillary wall interaction. In light of this result, the decision to add a significant organic component to the run buffer was made. The 50 mM aqueous citric acid solution was then diluted 1:2 with acetonitrile to produce a more suitable run buffer. When this new buffer was used in a CE separation run, the reduction in net citric acid concentration and the change in the dielectric constant were found to further reduce the average system current to 10 µA at +20 kV. This allowed for highly consistent electropherograms and minimal instances of total current loss. The change also resulted in nearly a 50-fold increase in the wave-mixing signal, as shown in FIG. 19B, when compared to that of 50 mM citric acid alone (FIG. 19A). This dramatic increase is due to a combination of effects. First, CV and MG both have greater absorptivity in acetonitrile than in water. Second, solubility of both compounds is increased in acetonitrile, which may have reduced capillary wall interactions and improved electrokinetic injections. Given the observations made with each of these capillary electrophoresis run buffers, the 50 mM citric acid: acetonitrile (1:2) solution was the clear choice in terms of signal response and system stability. This run buffer was used for all further capillary electrophoresis runs.

Field Amplified Sample Stacking

Sample preparation can have a major impact on separation and detection of analytes in capillary electrophoresis. Sample stacking is a preparation technique that aims at pre-concentration of analytes prior to separation to increase efficiency. There are numerous types of sample stacking procedures; however, many of these methods require complex control over the capillary system. Field amplified sample stacking (FASS) is a simple stacking method that can yield large increases in signal-to-noise ratio (S/N) with only minor system modifications. By injecting samples in a low-conductivity solvent, analytes experience a strong electric field, and therefore, migrate at an increased rate relative to those injected in higher conductivity solvents. Analytes in a low-conductivity zone slow once the interface with a high-conductivity run buffer is reached, which causes a stacking effect. Due to the limited injection capability of our capillary electrophoresis system, this technique was chosen for separation of MG and CV.

Figure 20:
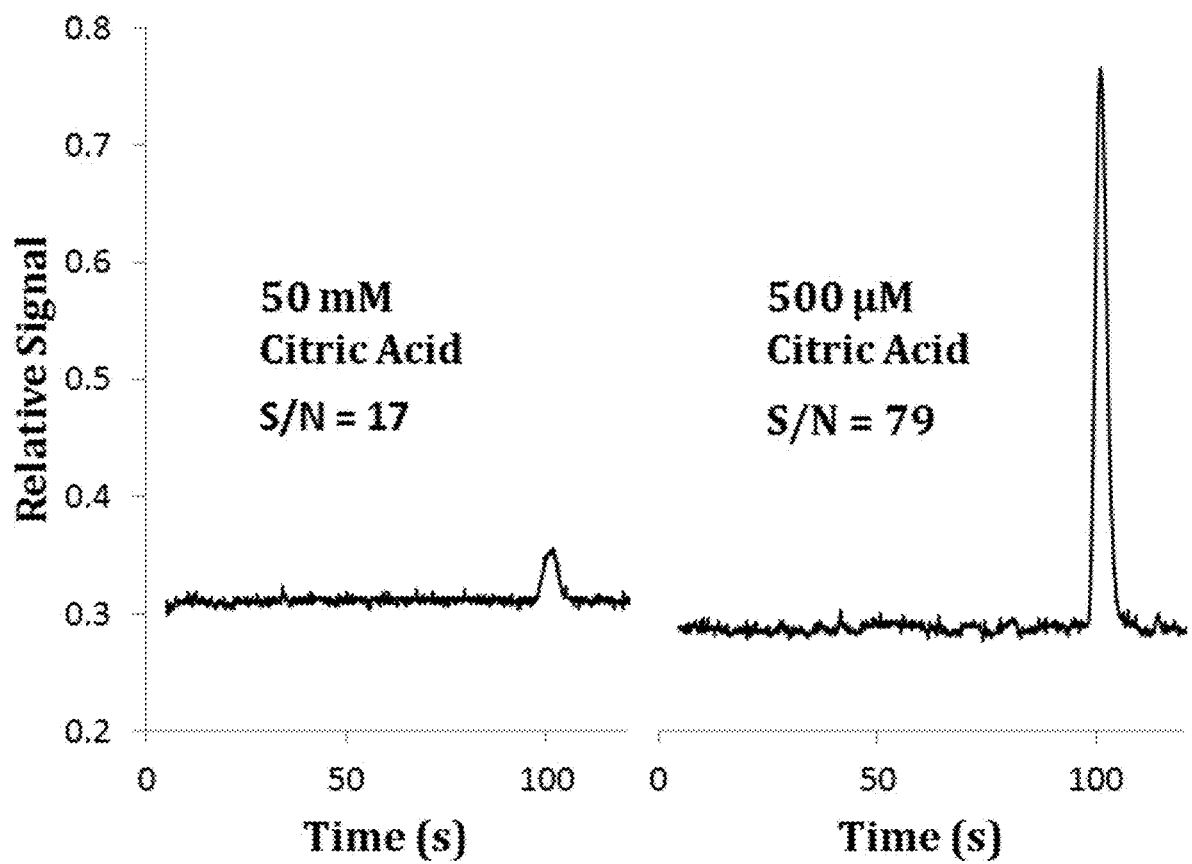
FIG. 20 shows electropherograms for 10 µM CV prepared in both 50 mM citric acid/acetonitrile (1:2) and 0.5 mM citric acid/acetonitrile (1:2).

FIG. 20 shows electropherograms for 10 µM CV prepared in both 50 mM citric acid/acetonitrile (1:2) and 0.5 mM citric acid/acetonitrile (1:2). The 50 mM citric acid/acetonitrile (1:2) was used as run buffer for both runs. The peaks obtained showed a dramatic difference in S/N, with the sample prepared in low-conductivity stacking buffer yielding nearly a 5-fold increase over the sample prepared in run buffer. Given this significant improvement in detection sensitivity, all further samples were prepared in 0.5 mM citric acid/acetonitrile (1:2) stacking buffer. To obtain results in FIG. 20, capillary electrophoresis has the following parameters: 20 kV, 75 µm i.d., 360 µm o.d., 40 cm capillary (20 cm effective length); 5 s electrokinetic injection.

Bare Capillary Separation

Figure 21:
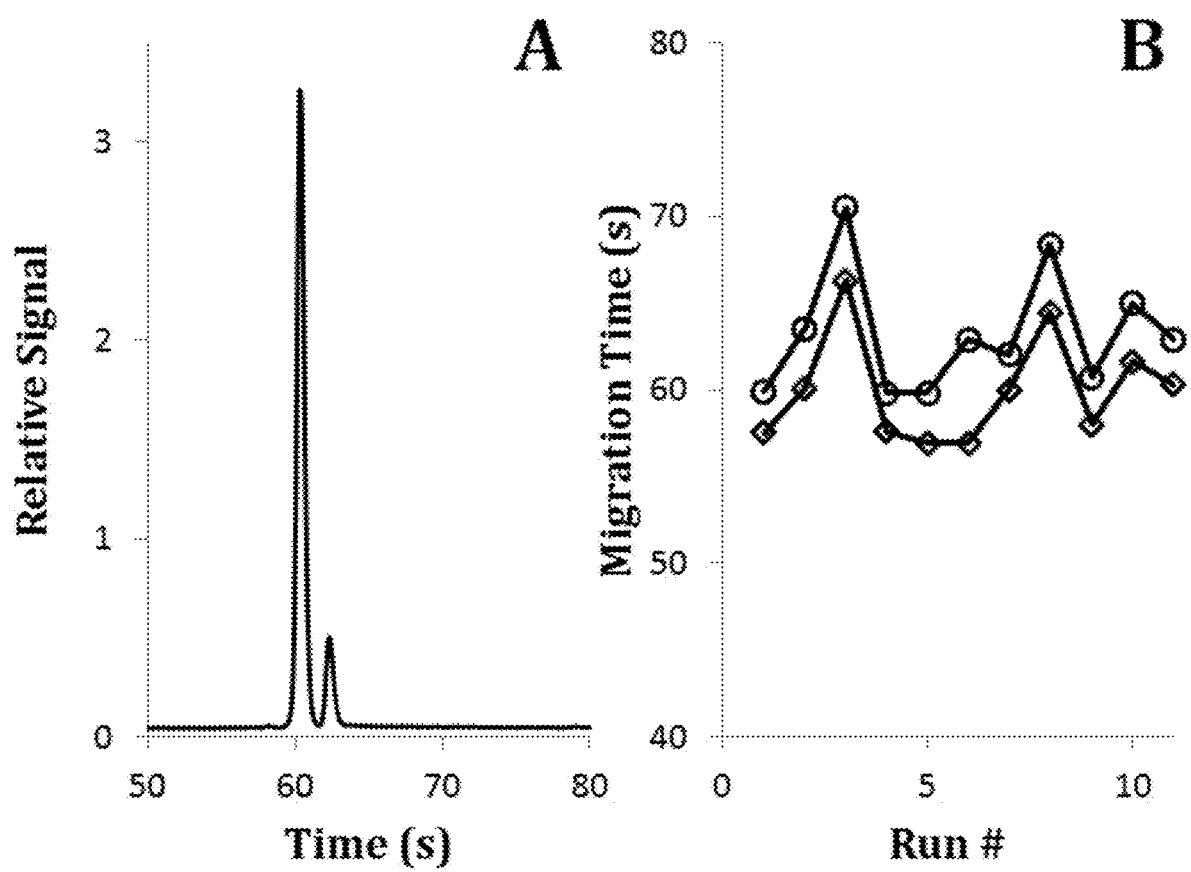
FIG. 21A shows electropherogram of a mixture of 10 µM MG and 10 µM CV in 0.5 mM aqueous citric acid/acetonitrile (1:2) stacking buffer
FIG. 21B shows migration times for repeated injections of the same sample mixture in FIG. 21A.

FIG. 21A shows a typical electropherogram for a mixture of 10 µM MG and 10 µM CV using capillary zone electrophoresis (CZE). The mixture of 10 µM MG and 10 µM CV is prepared in 0.5 mM aqueous citric acid/acetonitrile (1:2) stacking buffer. Eleven successive injections of the sample mixture were performed to observe variation in run-to-run migration times. Migration times for each compound showed good repeatability at 57-65 seconds (RSD of 5.2%) for MG and 60-71 seconds (RSD of 5.6%) for CV, as shown in FIG. 21B, despite a lack of temperature control or automated sample injection. In FIG. 21B, migration times for MG is shown with "○", and migration time for CV is shown with "◇." Capillary electrophoresis parameters used in FIGS. 21A and 21B are as follows: 20 kV, 100 µm i.d., 360 µm o.d., 35 cm capillary (17 cm effective length), 10 s electrokinetic injection. For all trials, both MG and CV peaks were resolved from one another; however, it was observed that after 3 to 4 runs, migration times for both compounds increased. This is most evident with the migration times for runs 3 and 8, which show a significant increase in relation to the previous run. Additional treatment of the capillary with 0.1 N NaOH was performed for 1 minute after each of these runs, and migration times were found to stabilize. This change in migration times is the result of re-protonation of capillary silanol groups due to the use of an acidic run buffer. Decreases in the net negative charge on the capillary surface reduce electroosmotic flow (EOF), while treatment with base serves to restore the net negative charge and EOF. Further reduction in run-to-run RSD may be obtained through flushing the capillary with 0.1 N NaOH between runs.

Another observation from this experiment is the difference in analyte wave-mixing signal strengths. The signal for MG is significantly stronger than that of CV due to two factors. First, the 635 nm laser has a greater effective power (65 mW) than that of the 532 nm laser (40 mW). Since wave-mixing signals have a cubic dependence on laser power, a higher intensity signal is generated for MG. Additionally, MG also absorbs at 532 nm allowing for signal formation from both input lasers. This amounts to total MG signal strength that is approximately 5 times greater than that generated by CV. The peaks shown in FIG. 21A reflect this difference.

Effects of Capillary Dynamic Coating

Although separation of MG and CV was successfully obtained using a bare fused-silica capillary, a degree of system control is required to prevent shifts in migration time from causing peak overlap between runs. To this end, modification of the CZE system could potentially allow for improved separation. One means of creating greater separation between analytes is through reduction of electroosmotic flow. Dynamic capillary coatings offer a simple means of EOF reduction through non-permanent alteration of the capillary surface.

Figure 22:
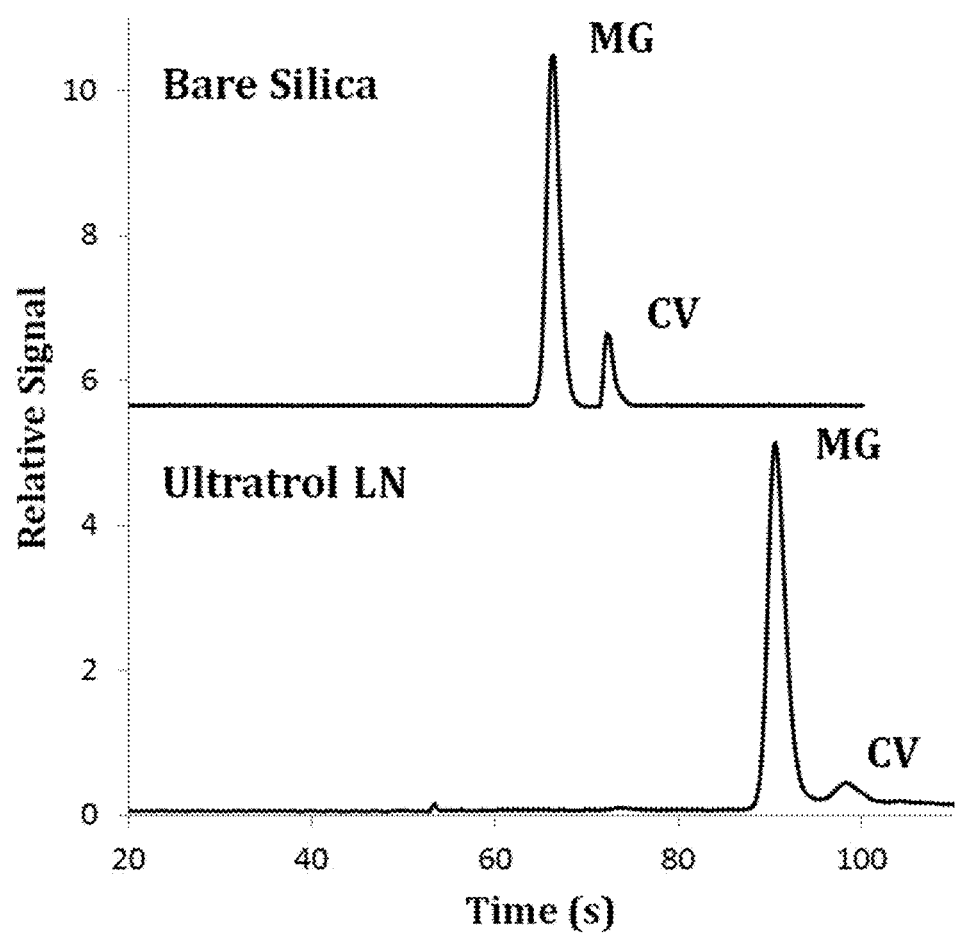
FIG. 22 shows electropherograms of a mixture of 10 µM MG and 10 µM CV in 0.5 mM aqueous citric acid/acetonitrile (1:2) stacking buffer.

FIG. 22 shows CE separation of MG and CV in a 100 μm i.d. capillary with and without Ultratrol LN dynamic coating. In the uncoated capillary, MG and CV were detected at 66.3 and 72.3 s. In FIG. 22, electropherograms of a mixture of 10 μM MG and 10 μM CV in 0.5 mM aqueous citric acid/acetonitrile (1:2) stacking buffer are analyzed. The top graph shows a case where bare fused silica capillary is used and the bottom graph shows another case where Ultratrol LN dynamic capillary coating is performed. The capillary electrophoresis parameters used in FIG. 22 are as follows: 20 kV, 100 μm i.d., 360 μm i.d., 35 cm capillary (17 cm effective length), 3 s electrokinetic injection. However, the addition of Ultratrol LN shifted these migration times to 90.6 and 98.4 s, respectively. This is a 30% improvement in migration time differential; however, there was no net gain in overall peak resolution with this modification. In both cases, band broadening negatively affected peak shape, which negated improvement in migration time change. For this reason, bare capillaries were used for further measurement of samples.

Detection Limits

Figure 23:
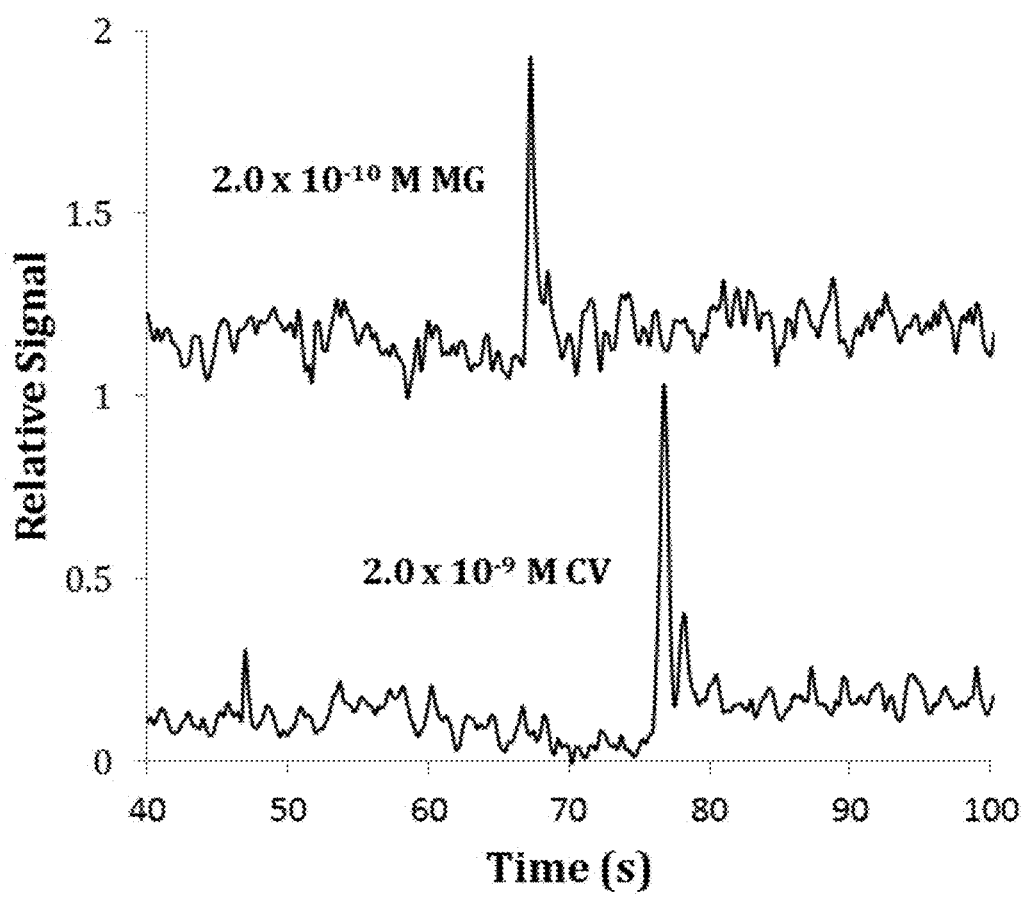
FIG. 23 shows electropherograms of 2.0×10-10 M MG and 2.0×10-9 CV in 0.5 mM aqueous citric acid/acetonitrile (1:2) stacking buffer.
Figure 24:
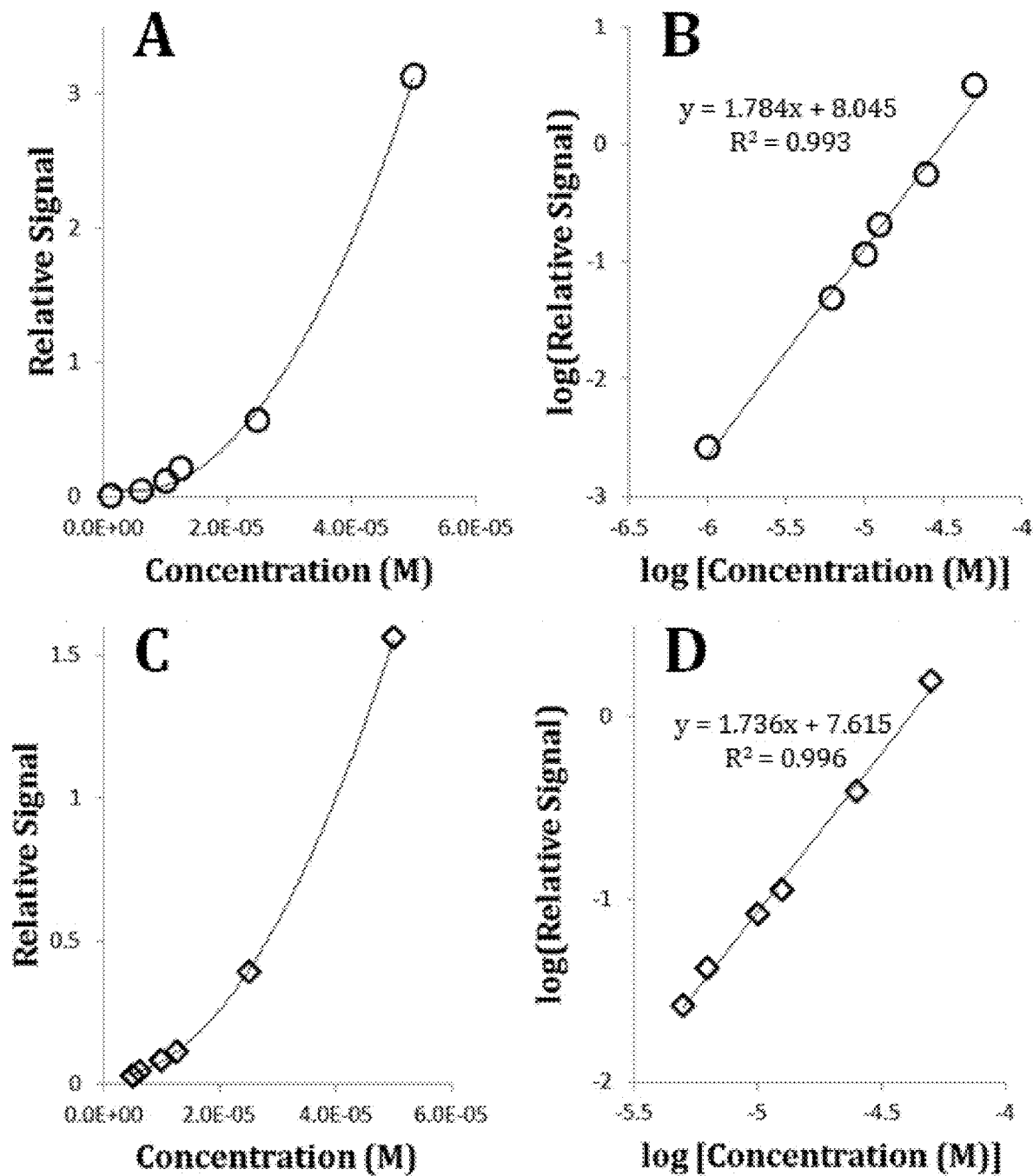
FIG. 24A shows a relationship between a relative signal and concentration for CV.
FIG. 24B shows a relationship between log(signal) and log(concentration) for CV.
FIG. 24C shows a relationship between a relative signal and concentration for MG.
FIG. 24D shows a relationship between a log(signal) and log(concentration) for MG.

To determine the lowest detectable concentration of both MG and CV, stock solutions were prepared at high concentration ($1.0 \times 10^{-3}$ M) in 0.5 mM aqueous citric acid/acetonitrile (1:2) stacking buffer. Serial dilutions were then made ranging from $1.0 \times 10^{-4}$ M to $1.0 \times 10^{-12}$ M and tested individually. It should be noted that after initial optical alignment with high concentration samples, no changes were made to the positions of mirrors, spatial filters or the sample cell. The only changes made during this process were to detector gain and signal amplification scaling. FIG. 23 shows the lowest concentration MG and CV samples ($2.0 \times 10^{-10}$ M MG and $2.0 \times 10^{-9}$ M CV) that generated a detectable wave-mixing signal. In FIG. 23, $2.0 \times 10^{-10}$ M MG and $2.0 \times 10^{-9}$ M CV is prepared in 0.5 mM aqueous citric acid/acetonitrile (1:2) stacking buffer. Capillary electrophoresis parameters used in FIG. 23 are as follows: 20 kV, 100 i.d., 360 μm o.d., 35 cm capillary (17 cm effective length); 15 s electrokinetic injection. From these electropherograms, the limits of detection were calculated using peak height (signal) and the standard deviation of the baseline (noise). Preliminary concentration detection limits of $8.3 \times 10^{-11}$ M for MG and $6.9 \times 10^{-10}$ M for CV (S/N=2) were determined. Using an estimated laser probe volume of 360 pL, preliminary mass detection limits of $3.0 \times 10^{-20}$ mol for MG and $2.5 \times 10^{-19}$ mol for CV were determined. The sample size detected is very small, since wave mixing only requires a micrometer thin optical path length and the focused laser beam diameter is smaller 70 μm.

Investigation of the technique as a quantitative tool led to generation of standard curves using a series of MG and CV calibrators. For each set of calibrators, instrument response vs. analyte concentration was characterized. Instead of electrokinetic injection, each sample was drawn into a 75 μm i.d., 360 μm o.d., 40 cm capillary using a peristaltic pump at a continuous flow rate of 5 μL/min. Wave-mixing signal produced by each sample was monitored over a 30 second period (10 data points/s). This allowed for direct evaluation of wave-mixing signal linearity without variation introduced by the capillary electrophoresis system. Future method development using commercially-available capillary electrophoresis instruments coupled with our wave-mixing detector is expected to allow for traditional linearity assessment under controlled electrophoretic conditions.

The mean signal values obtained for 1.0-50 μM CV samples are shown in FIG. 24A. Given the square dependence of wave-mixing signal on absorptivity, a second-order polynomial response was observed. On a logarithmic scale, a slope of approximately 2 was observed as expected (FIG. 24B). Linear fit over this range was found to be good, with the relationship defined as y=1.784x+8.045 ($R^2$=0.993). Similarly, FIG. 24C and FIG. 24D illustrate mean wave-mixing signals for 6.25-50 μM MG calibrator samples on both absolute and logarithmic scales. Linear line fit for these samples also resulted in a high correlation coefficient (y=1.736x+7.615, $R^2$=0.996).

Laser wave mixing coupled with capillary electrophoresis provides a highly sensitive detection method for malachite green and crystal violet. The method does not require any derivatization or labeling of the target analytes, and it is capable of producing reproducible results in less than two minutes. It yields picomolar detection limits in a detection system that can be scaled down to field-deployable designs, while other published techniques do not offer both sensitivity and portability, as shown in Table 2 and Table 3. Further development of this method may offer even greater sensitivity and reproducibility through more advanced sample stacking techniques and enhanced system controls.

TABLE 2

Detection limits for crystal violet detection methods.

| Method | Detection Limit |
| --- | --- |
| LC-QqQLIT-MS/MS | $3.29 \times 10^{-11}$ M (12.2 ppt) |
| LC-ESI-MS/MS | $4.1 \times 10^{-10}$ M (152 ppt) |
| CE-D4WM | $6.9 \times 10^{-10}$ M (256 ppt) |
| ELISA | $1.01 \times 10^{-9}$ M (374 ppt) |
| LC-MS/MS | $2.2 \times 10^{-9}$ M (815 ppt) |
| SPE-UV/Vis | $1.23 \times 10^{-9}$ M (456 ppt) |
| CE - UV/Vis | $9.8 \times 10^{-8}$ M (36.3 ppb) |

TABLE 3

Detection limits for malachite green detection methods.

| Method | Detection Limit |
| --- | --- |
| TiO$_2$ SERS Sensor | $1 \times 10^{-12}$ M (0.3 ppt) |
| LC-QqQLIT-MS/MS | $3.29 \times 10^{-11}$ M (10.8 ppt) |
| CE-D4WM | $8.3 \times 10^{-11}$ M (27.3 ppt) |
| LC-DAD | $1.08 \times 10^{-10}$ M (35.6 ppt) |
| LC-ESI-MS/MS | $4.1 \times 10^{-10}$ M (135 ppt) |
| ELISA | $6.33 \times 10^{-10}$ M (209 ppt) |
| LC-IT-MS | $6.85 \times 10^{-10}$ M (226 ppt) |

The above examples demonstrate a highly sensitive test method for simultaneous detection of malachite green and crystal violet has been achieved. The method is compatible with existing extraction techniques provided filtration and dialysis into the appropriate sample buffers, and it may also be used to detect the metabolites leuco malachite green and leuco crystal violet if samples are oxidized used published sample preparation methods.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is what is described and illustrated, including:

1. A method for measuring α-synuclein in a body fluid of a patient with high detection sensitivity and accuracy and providing early stage Parkinson's disease detection, comprising:
   supplying to a capillary analyte cell a fluidic sample that includes a body fluid of a patient containing α-synuclein, wherein the capillary analyte cell is located in a nonlinear optical four-wave mixing device;
   directing laser light from the nonlinear optical four wave-mixing device into the capillary analyte cell to cause nonlinear optical four-wave mixing in the fluidic sample to generate a four wave-mixing signal that contains information on the α-synuclein in the fluidic sample;

processing the four wave-mixing signal to extract information on the α-synuclein in the fluidic sample; and
using the extracted information to determine the patient's condition in connection with the Parkinson's disease.

2. The method as in claim 1, comprising:
using a cerebrospinal fluid that was obtained, prior to preforming the method, from the patient to form the fluidic sample, to obtain the four-wave mixing signal.

3. The method as in claim 1, comprising:
using blood that was obtained, prior to preforming the method, from the patient to form the fluidic sample, to obtain the four-wave mixing signal.

4. The method as in claim 1, further comprising, prior to the directing of the laser light, based on an absorption spectrum of α-synuclein:
obtaining UV-visible absorption spectra of laser light to determine a wavelength of laser light used in the nonlinear optical four-wave mixing device.

5. The method as in claim 1, wherein the supplying of the fluidic sample includes:
conjugating α-synuclein with a label including fluorescein isothiocyanate (FITC), QSY 35, or Chromeo P503.

6. The method as in claim 5, wherein the supplying of the fluidic sample includes:
determining a protein-label reaction ratio indicating concentration of the label with respect to α-synuclein.

7. The method as in claim 1, wherein the supplying of the fluidic sample includes:
applying a dynamic coating to the capillary analyte cell.

8. The method as in claim 1, wherein the processing of the four wave-mixing signal includes:
identifying oligomeric form of α-synuclein to perform molecular weight-based separation.

9. A system for diagnosing a person's condition in connection with the Parkinson's disease, comprising:
a microfluidic system that includes a capillary analyte cell that is coupled to receive a fluidic sample that includes a body fluid of a patient containing α-synuclein;
a nonlinear optical four-wave mixing device that includes a laser that produces laser beams for nonlinear four-wave mixing, optical elements that direct the laser beams to a selected location in the capillary analyte cell where the laser beams intercept with one another to interact with the fluidic sample in the capillary analyte cell to cause nonlinear wave mixing that generates a four-wave mixing signal that contains information on the α-synuclein in the fluidic sample, and an optical detector that receives the four-wave mixing signal and converts the received four-wave mixing signal to a detector signal; and
a processing module that processes the detector signal to extract information on the α-synuclein in the fluidic sample and uses the extracted information to determine the patient's condition in connection with the Parkinson's disease.

10. The system as in claim 9, wherein:
the microfluidic system supplies a cerebrospinal fluid from the patient to the fluidic sample.

11. The system as in claim 9, wherein:
the microfluidic system supplies blood from the patient to form the fluidic sample.

12. The system as in claim 9, wherein the nonlinear optical four-wave mixing device allows label-free detection of a native form of α-synuclein.

13. The system as in claim 9, wherein α-synuclein is conjugated with labels including at least one of fluorescein isothiocyanate (FITC), QSY 35, or Chromeo P503.

14. The system as in claim 9, wherein the capillary analyte cell includes a dynamic coating polymer.

15. A method for measuring a low concentration level of a suspect substance including at least one of Malachite Green or Crystal Violet with high detection sensitivity and accuracy, comprising:
supplying to a capillary electrophoresis system a fluidic sample that includes a low concentration of at least one suspect substance within a nonlinear optical four-wave mixing device;
directing laser light from the nonlinear optical four-wave mixing device into the fluidic sample to cause nonlinear optical four-wave mixing in the fluidic sample to generate a four-wave mixing signal that contains information on the low concentration of the at least one suspect substance in the fluidic sample; and
processing the four-wave mixing signal to extract information on the at least one suspect substance in the fluidic sample,
wherein the directing of laser light includes, if the fluid sample includes a single suspect substance: using a laser with an off-resonant wavelength to excite the single suspect sub stance.

16. The method as in claim 15, wherein the directing of laser light includes, if the fluid sample includes two or more suspect substances:
using multiple lasers of different wavelengths to excite the two or more suspect substances.

17. The method as in claim 15, further comprising:
performing pre-concentration of the at least one suspect substance using filed amplified sample stacking (FASS).

18. The method as in claim 15, wherein the processing of the four-wave mixing signal includes identifying the at least one suspect substance at sub-nanomolar concentrations.

19. A method for measuring a low concentration level of a suspect substance including at least one of Malachite Green or Crystal Violet with high detection sensitivity and accuracy, comprising:
supplying to a capillary electrophoresis system a fluidic sample that includes a low concentration of at least one suspect substance within a nonlinear optical four-wave mixing device;
directing laser light from the nonlinear optical four-wave mixing device into the fluidic sample to cause nonlinear optical four-wave mixing in the fluidic sample to generate a four-wave mixing signal that contains information on the low concentration of the at least one suspect substance in the fluidic sample;
processing the four-wave mixing signal to extract information on the at least one suspect substance in the fluidic sample; and
applying a dynamic coating to the capillary electrophoresis system to reduce electroosmotic flow (EOF).

20. A device for measuring a low concentration level of a suspect substance including at least one of Malachite Green or Crystal Violet with high detection sensitivity and accuracy, comprising:
a microfluidic system that is coupled to receive a fluidic sample that includes a low concentration of a suspect substance;
a nonlinear optical four-wave mixing device that includes a laser that produces laser beams for nonlinear four-wave mixing, optical elements that direct the laser beams to a selected location in microfluidic system where the laser beams intercept with one another to interact with the fluidic sample to cause nonlinear wave mixing that generates a four-wave mixing signal that contains information on the suspect substance in the fluidic sample, and an optical detector that receives the four-wave mixing signal and converts the received four-wave mixing signal to a detector signal; and a processing module that processes the detector signal to extract information on the suspect substance in the fluidic sample, wherein the laser has an off-resonant wavelength different from a peak absorption wavelength of the suspect substance.

21. The device as in claim 20, wherein the microfluidic system includes a capillary electrophoresis device using citric acid or another agent.

22. The device as in claim 20, wherein the microfluidic system includes a capillary with a dynamic coating.

23. The device as in claim 20, wherein the processing module performs an evaluation of a linearity of the four-wave mixing signal.

24. A system for measuring a low concentration level of a suspect substance, comprising:

a nonlinear optical wave-mixing device using lasers with different wavelengths from each other that are shifted from absorption peaks of analytes; and a capillary electrophoresis device coupled with the nonlinear optical wave-mixing device and migrating the analytes through electrolyte solutions under an electric field, the migration of the analytes providing information used to detect at least one of the analytes, wherein the nonlinear optical wave-mixing device and the capillary electrophoresis are packaged together to provide a portability.

25. The system of claim 24, wherein each wavelengths of the lasers are selected to the analytes to use dual-wavelength cross verification.

26. The system of claim 24, wherein the device provides real-time dynamic measurements of the analytes.

27. The system of claim 24, wherein the capillary electrophoresis includes a capillary with a dynamic coating.

* * * * *

UNITED STATES PATENT AND TRADEMARK OFFICE
CERTIFICATE OF CORRECTION

PATENT NO. : 11,333,667 B2
APPLICATION NO. : 15/999856
DATED : May 17, 2022
INVENTOR(S) : William G. Tong Page 1 of 1

It is certified that error appears in the above-identified patent and that said Letters Patent is hereby corrected as shown below:

In the Specification

In the Statement Regarding Federally Sponsored Research or Development, in Column 1, Line 21 delete "Part of the inventions in this patent document was made with United States government support under Grant Nos. 5-R01-GM41032 and 2R25GM058906-13 awarded by the National Institutes of Health (NIH)/National Institute of General Medical Sciences (NIGMS). In addition, part of the inventions was made with United States government support by the National Institute of General Medical Sciences, National Institutes of Health under Grant 5-R01-GM41032, the National Science Foundation, the U.S. Department of Homeland Security Science and Technology Directorate, the U.S. Department of Defense (CCAT), the Army Research Office, and the NIH NIGMS SDSU IMSD Program Grant 2R25GM058906-13. The United States government has certain rights in the inventions."

And insert -- This invention was made with government support under grant numbers GM041032, GM058906 awarded by the National Institutes of Health. The government has certain rights in the invention. --, therefor.

Signed and Sealed this
Twenty-ninth Day of April, 2025

Coke Morgan Stewart
*Acting Director of the United States Patent and Trademark Office*

```
                        SEQUENCE LISTING

<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```